(12) United States Patent
Xiao et al.

(10) Patent No.: US 8,912,353 B2
(45) Date of Patent: Dec. 16, 2014

(54) ORGANOAMINOSILANE PRECURSORS AND METHODS FOR DEPOSITING FILMS COMPRISING SAME

(75) Inventors: Manchao Xiao, San Diego, CA (US); Mark Leonard O'Neill, San Marcos, CA (US); Heather Regina Bowen, Vista, CA (US); Hansong Cheng, Singapore (SG); Xinjian Lei, Vista, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 115 days.

(21) Appl. No.: 13/114,287

(22) Filed: May 24, 2011

(65) Prior Publication Data

US 2012/0128897 A1   May 24, 2012

Related U.S. Application Data

(60) Provisional application No. 61/350,750, filed on Jun. 2, 2010.

(51) Int. Cl.
*C07F 7/02* (2006.01)
*C23C 16/34* (2006.01)
*C23C 16/40* (2006.01)

(52) U.S. Cl.
CPC ............. *C07F 7/025* (2013.01); *C23C 16/345* (2013.01); *C23C 16/401* (2013.01)
USPC ........................................................ 556/410

(58) Field of Classification Search
CPC ........... C07F 7/10; C07F 7/025; C07F 7/1868
USPC ........................................................ 556/410
See application file for complete search history.

(56) References Cited

U.S. PATENT DOCUMENTS

| | | | |
|---|---|---|---|
| 4,200,666 A | 4/1980 | Reinberg | |
| 4,863,755 A | 9/1989 | Hess et al. | |
| 4,916,828 A | 4/1990 | Yamane et al. | |
| 4,992,299 A | 2/1991 | Hochberg et al. | |
| 5,008,422 A | 4/1991 | Blum et al. | |
| 5,234,869 A | 8/1993 | Mikata et al. | |
| 5,250,473 A | 10/1993 | Smits | |
| 5,382,550 A | 1/1995 | Iyer | |
| 5,458,689 A | 10/1995 | Saito | |
| 5,622,784 A | 4/1997 | Okaue et al. | |
| 5,656,076 A | 8/1997 | Kikkawa | |
| 5,772,757 A | 6/1998 | Saito | |
| 5,837,056 A | 11/1998 | Kikkawa | |
| 5,874,368 A | 2/1999 | Laxman et al. | |
| 6,153,261 A | 11/2000 | Xia et al. | |
| 6,268,299 B1 | 7/2001 | Jammy et al. | |
| 6,391,803 B1 | 5/2002 | Kim et al. | |
| 6,486,015 B1 | 11/2002 | Chaudhary et al. | |
| 6,486,083 B1 | 11/2002 | Mizuno et al. | |
| 6,500,772 B2 | 12/2002 | Chakravarti et al. | |
| 6,559,074 B1 | 5/2003 | Chen et al. | |
| 6,586,056 B2 | 7/2003 | Arkles et al. | |
| 6,630,413 B2 | 10/2003 | Todd | |
| 6,716,772 B2 | 4/2004 | Mizuno et al. | |
| 6,890,869 B2 | 5/2005 | Chung | |
| 6,913,029 B2 | 7/2005 | Zorich et al. | |
| 6,974,780 B2 | 12/2005 | Schuegraf | |
| 7,084,076 B2 | 8/2006 | Park et al. | |
| 7,098,150 B2 | 8/2006 | Misra et al. | |
| 7,122,222 B2 | 10/2006 | Xiao et al. | |

(Continued)

FOREIGN PATENT DOCUMENTS

CN       1356181 A       7/2002
EP       0 481 706 A1    4/1992

(Continued)

OTHER PUBLICATIONS

C. Glidewell and D. W. H. Rankin, "Some Preparative and Spectroscopic Studies of Silylamines" J. Chem. Soc. (A), (1970), (2), 279-86.*

A.N. Egorochkin. et al, Interaction in Bonds of Silicon with Nitrogen and Phosphorus, Izvestiya Akademii Nauk SSSR, Seriya Khimicheskaya, 1970, 2609-2611.*

R.G. Gordon, et al, Silicon Dimethylamido Complexes and Ammonia as Precursors for the Atmospheric Pressure Chemical Vapor Deposition of Silicon Nitride Thin Films, American Chemical Society, 1990, 480-482.

(Continued)

*Primary Examiner* — Fereydoun G Sajjadi
*Assistant Examiner* — Kofi Adzamli
(74) *Attorney, Agent, or Firm* — Rosaleen P. Morris-Oskanian

(57) ABSTRACT

Described herein are precursors and methods of forming dielectric films. In one aspect, there is provided a silicon precursor having the following formula I:

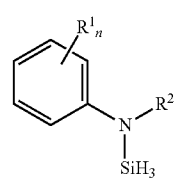

wherein $R^1$ is independently selected from hydrogen, a linear or branched $C_1$ to $C_6$ alkyl, a linear or branched $C_2$ to $C_6$ alkenyl, a linear or branched $C_2$ to $C_6$ alkynyl, a $C_1$ to $C_6$ alkoxy, a $C_1$ to $C_6$ dialkylamino and an electron withdrawing group and n is a number selected from 0, 1, 2, 3, 4, and 5; and $R^2$ is independently selected from hydrogen, a linear or branched $C_1$ to $C_6$ alkyl, a linear or branched $C_2$ to $C_6$ alkenyl, a linear or branched $C_2$ to $C_6$ alkynyl, a $C_1$ to $C_6$ alkoxy, a $C_1$ to $C_6$ dialkylamino, a $C_6$ to $C_{10}$ aryl, a linear or branched $C_1$ to $C_6$ fluorinated alkyl, and a $C_4$ to $C_{10}$ cyclic alkyl group.

57 Claims, 11 Drawing Sheets

(56) References Cited

U.S. PATENT DOCUMENTS

| | | | |
|---|---|---|---|
| 7,125,582 | B2 | 10/2006 | McSwiney et al. |
| 7,172,792 | B2 | 2/2007 | Wang et al. |
| 7,332,618 | B2 | 2/2008 | Meiere |
| 7,351,670 | B2 | 4/2008 | Hoshi et al. |
| 7,365,029 | B2 | 4/2008 | Iyer et al. |
| 7,446,217 | B2 | 11/2008 | Wang et al. |
| 7,462,376 | B2 | 12/2008 | Kato et al. |
| 7,473,655 | B2 | 1/2009 | Wang et al. |
| 7,482,286 | B2 | 1/2009 | Misra et al. |
| 7,510,984 | B2 | 3/2009 | Saito et al. |
| 7,531,679 | B2 | 5/2009 | Wang et al. |
| 7,651,961 | B2 | 1/2010 | Clark et al. |
| 7,713,346 | B2 | 5/2010 | Wang et al. |
| 7,786,320 | B2 | 8/2010 | Wang et al. |
| 7,875,556 | B2 | 1/2011 | Xiao et al. |
| 7,999,355 | B2 | 8/2011 | Weigel |
| 2002/0086541 | A1 | 7/2002 | Fu et al. |
| 2002/0175393 | A1 | 11/2002 | Baum et al. |
| 2003/0124818 | A1 | 7/2003 | Luo et al. |
| 2005/0048204 | A1 | 3/2005 | Dussarrat et al. |
| 2005/0085098 | A1 | 4/2005 | Timmermans et al. |
| 2005/0163927 | A1 | 7/2005 | McSwiney et al. |
| 2006/0022803 | A1 | 2/2006 | Akiyama et al. |
| 2006/0045986 | A1 | 3/2006 | Hochberg et al. |
| 2006/0051975 | A1 | 3/2006 | Misra et al. |
| 2006/0062913 | A1 | 3/2006 | Wang et al. |
| 2006/0099831 | A1 | 5/2006 | Borovik et al. |
| 2006/0216950 | A1 | 9/2006 | Matsuura |
| 2006/0228903 | A1 | 10/2006 | McSwiney et al. |
| 2006/0258173 | A1 | 11/2006 | Xiao et al. |
| 2007/0160774 | A1 | 7/2007 | Tsukada et al. |
| 2007/0275166 | A1 | 11/2007 | Thridandam et al. |
| 2008/0038936 | A1 | 2/2008 | Todd et al. |
| 2008/0124946 | A1 | 5/2008 | Xiao et al. |
| 2008/0207007 | A1 | 8/2008 | Thridandam et al. |
| 2008/0260969 | A1 | 10/2008 | Dussarrat et al. |
| 2009/0041952 | A1 | 2/2009 | Yoon et al. |
| 2009/0069588 | A1 | 3/2009 | Xiao et al. |
| 2009/0075490 | A1 | 3/2009 | Dussarrat |
| 2009/0205568 | A1 | 8/2009 | Mizuno et al. |
| 2010/0009546 | A1 | 1/2010 | Weigel et al. |
| 2010/0209624 | A1 | 8/2010 | Matsuura |

FOREIGN PATENT DOCUMENTS

| | | |
|---|---|---|
| EP | 1149934 | 8/2005 |
| EP | 1 967 609 A2 | 9/2008 |
| GB | 1123252 | 8/1968 |
| JP | 6132276 | 5/1994 |
| JP | 06132284 | 5/1994 |
| JP | 07235535 | 9/1995 |
| JP | 8227890 | 9/1996 |
| JP | 00195801 | 7/2000 |
| JP | 2001156063 | 6/2001 |
| JP | 200526244 | 1/2005 |
| KR | 1020050018641 | 2/2006 |
| WO | 0265508 | 8/2002 |
| WO | 2004010467 | 1/2004 |
| WO | 2004017383 | 2/2004 |
| WO | 2004030071 | 4/2004 |
| WO | 2005080628 | 9/2005 |
| WO | 2005093126 | 10/2005 |
| WO | 2006036538 | 4/2006 |
| WO | 2006097525 | 9/2006 |
| WO | 2008028170 | 6/2008 |

OTHER PUBLICATIONS

D.M. Hoffman, et al, Plasma enhanced chemical vapor deposition of silicon nitride films from a metal-organic precursor, Materials Research Society, 1994, 3019-3021.
A. Kikkawa, et al, Electrical properties of silicon nitride films deposited by catalytic chemical vapor deposition on catalytically nitrided Si(100), Thin Solid Films, 2003, 100-103.
S. Yokoyama, et al, Atomic-layer selective deposition of silicon nitride on hydrogen-terminated Si surfaces, Applied Surface Science, 1998, 352-356.
Nekrasov, Y.S., et al.; "On the Relationship between the Mass Spectral and Structural Indices of Arylsilanes"; Russian Chemical Bulletin; vol. 42, No. 2; Feb. 1993; pp. 343-346.
Egorochkin, A.N., et al. "d(pi)-p(pi) Interaction in Bonds of Silicon with Nitrogen and Phosphorus"; Bulletin of the Academy of Sciences of the USSR, Div of Chemical Sciences; vol. 19, No. 11; Nov. 1970; pp. 2454-2456.
Glidewell, C. et al.; "Some Preparative and Spectroscopic Studies of Silylamines"; Journals of the Chemical Society. A. Inorganic, Physical and Theoretical Chemistry; 1970; pp. 279-286.
Aylett, B.J., et al.; "Silicon Nitrogen Compounds. Part VII. N-Silyl Derivatives of Aniline"; Journals of the Chemical Society. A, Inorganic, Physical and Theoretical Chemistry; 1969; pp. 800-803.
Aylett, B.J., et al.; "Silicon Nitrogen Compounds. Part VI. The Preparation and Properties of Disilazane"; Journals of the Chemical Society. A, Inorganic, Physical and Theoretical Chemistry; 1969; pp. 639-642.
Aylett, B.J., et al.; "Silicon Nitrogen Compounds. Part V. Diphynlamino-Derivatives of Silane"; Journals of the Chemical Society. A, Inorganic, Physical and Theoretical Chemistry; 1969; pp. 636-638.
Gary E. McGuire, Semiconductor Materials and Process Technology Handbook, Noyes Publications, NJ, 1988, pp. 239-301.
Stanley Wolf, Silicon Processing for the VLSI Era, Lattice Press, CA 1990, pp. 327-330.
Arthur K. Hochberg, et al, Diethylsilane as a Source for the Deposition . . ., Mat. Res. Soc, Symp. Proc., vol. 204, 1991, pp. 509-513.
Tetsuji Sorita, et al, Mass Spectrometric and Kinetic Study of Low-Pressure . . ., J. Elec. Soc., vol. 141, No. 12, 1994, pp. 3506-3511.
B.J. Aylett, et al, the Preparation and Properties of Dimethylamino- and.., J. Chem. Soc. (A), 1967, pp. 652-655.
Sei Sujishi, et al, Effect of Replacement of Carbon by Silicon in Trimethylamine . . ., J. Am. Chem. Soc., vol. 78, 1956, pp. 4631-4636.
Kenneth Hedberg, The Molecular Structure of Trisilylamine (SiH3) 3N1, 2, J. Am. Chem. Soc., 1955, vol. 77, pp. 6491-6492.
J.M. Grow, et al, Growth Kinetics and Characterization of Low Pressure . . ., Mat. Letters vol. 23, 1995, pp. 187-193.
B.A. Scott, et al, Preparation of Silicon Nitride with Good Interface . . ., Chemtronics, 1989, vol. 4, pp. 230-233.
B.J. Aylett, et al, Silicon-Nitrogen Compounds. Part V. Diphenylamino-derivatives of Silane, J. Chem. Soc., 1989, 636-639.
Norbert W. Mizel, Simple Silylhydrazines as Models for Si-N.beta.-donor Interactions in SiNN Units, Chemistry-A European Journal, 1998, 692-698.
Hubert Schmidbuar, et al, Differences in Reactivity of 1,4-Disilabutane and N-Tetrasilane Towards Secondary Amines, Zeitschrift Fur Naturforschung B: Chemical Sciences, 1990, 1679-1683.
A.V. Golubinszkij, et al, Molecular-structure Examination of Some Organic Silicon Compounds by Electron Diffraction, Kemiai Kozlemenyek, 46, 1976, 473-480.
C. Glidewell, et al, Electron Diffraction Determination of the Molecular Structure of Tetrasilylhydrazine, Journal of the Chemical Society, 1970, 318-320.
H. Beck, et al, Radical Ions. 36. Structural Changes Accompanying the One-Electron Oxidation of Hydrazine and Its Silyl Derivatives)-3, Journal of the American Chemical Society, 1980, 4421-4428.
B.J. Aylett, The Silyl Group as an Electron Acceptor, J. Inorg. Nucl. Chem., 1956, 325-329.
N. Bingo, et al, Correlations Among X-H Bond Lengths, X-H Stretching Frequencies, and Bond Order Matrix Elements P HX: where X=C, N, and Si. J. Sci. Hiroshima Univ., 1976, 317-326.
B.J. Aylett, Vibrational spectra and structure of tetrasilylhydrazine and tetrasilylhydrazine-d, Spectrochimica Acta, 1960, 747-758.
C. Glidewell, et al, Some Preparative and Spectroscopic Studies of Silylamines, Journal of the Chemical Society a Inorg. Phys. Theor., 1970, 279-286.
B.J. Aylett, et al, N-Silyl Derivatives of Cyclic Secondary Amines, J. Chem. Soc, 1967, 1918-1921.

(56) References Cited

OTHER PUBLICATIONS

B.J. Aylett, et al, Silicon-Nitrogen Compounds. Part VIII. Base-Promoted Disproportionation of N-Methly- and N-Phenyl-Disilazane, J. Chem. Soc., 1969, 1788-1792.

D. Anderson, et al, Isopropyldisilylamine and Disilyl-t-butylamine: Preparation, Spectroscopic Properties, and Molecular Structure in the Gas Phase, determined by Electron Diffraction, J. Chem. Soc., 1989, 779-783.

A.N. Egorochkin, et al, Interation in Bonds of Silicon with Nitrogen and Phosphorus, Izvestiya Akademii Nauk SSSR, Seriya Khimicheskaya, 1970, 2609-2611.

Burton, B. B., et al, "Rapid SiO2 Atomic Layer Deposition Using Tris(tert-pentoxy)silanol", Chem. Mater., 20, 2008, 7031-7043.

Burton, B. B. et al, "SiO2 Atomic Layer Deposition Using Tris(dimethylamino)silane and Hydrogen Peroxide Studied by in Situ Transmission FTIR Spectroscopy", The Journal of Physical Chemistry, 113, 2009, 8249-8257.

Ferguson, J. D., et al, "ALD of SiO2 at Room Temperature Using TEOS and H2O with NH(3) as the Catalyst", Journal of the Electrochemical Society, 151, 2004, G528-G535.

Hirose, F., et al, Low-temperature-atomic-layer-deposition of SiO2 with Tris(dimethylamino)Silane (TDMAS) and Ozone using a Temperature Controlled Water Vapor Treatment, 215th ECS Meeting, 2009, San Francisco, CA.

I. Suzuki, et al, "Extra Low-Temperature SiO2 Deposition Using Aminosilanes", ECS Transactions 3(15), 007, 119-128.

Kamiyama, S., et al, "Comparison between SiO2 films deposited by atomic layer deposition with SiH2[N(CH3)2]2 and SiH[N(CH3)2]3 precursors", Thin Solid Films, 515(4), 2006, 1517-1521.

Lee, S., et al, "Atomic Layer Deposition of Silicon Oxide Thin Films by Alternating Exposures to Si2Cl6 and O3", Electrochemical and Solid-State Letters, 11(7), 2008, G23-G26.

Sneh, O., et al, "Atomic layer growth of SiO2 on Si(100) using SiCl4 and H2O in a binary reaction sequence", Surface Science, 334(1-3), 1995, 135-152.

\* cited by examiner

ORGANOAMINOSILANE PRECURSORS AND METHODS FOR DEPOSITING FILMS COMPRISING SAME

CROSS-REFERENCE TO RELATED APPLICATIONS

This application claims the priority benefit under 35 U.S.C. §119 of the following application: U.S. Provisional Application No. 61/350,750 filed 2 Jun. 2010.

BACKGROUND OF THE INVENTION

Precursors, particularly organoaminosilane precursors that can be used for the deposition of dielectric films, including but not limited to, silicon containing films such as silicon nitride, silicon oxide, silicon carbo-nitride, and silicon oxynitride films are described herein. In yet another aspect, described herein is the use of the organoaminosilane precursors for depositing silicon-containing dielectric films in the fabrication of integrated circuit devices. In these or other aspects, the organoaminosilane precursors may be used for a variety of deposition processes, including but not limited to, atomic layer deposition ("ALD"), chemical vapor deposition ("CVD"), plasma enhanced chemical vapor deposition ("PECVD"), low pressure chemical vapor deposition ("LPCVD"), and atmospheric pressure chemical vapor deposition.

Several classes of compounds can be used as precursors for silicon-containing films such as, but not limited to, silicon oxide or silicon nitride films. Examples of these compounds suitable for use as precursors include silanes, chlorosilanes, polysilazanes, aminosilanes, and azidosilanes. Inert carrier gas or diluents such as, but not limited, helium, hydrogen, nitrogen, etc., are also used to deliver the precursors to the reaction chamber.

Low pressure chemical vapor deposition (LPCVD) processes are one of the more widely accepted methods used by semiconductor industry for the deposition of silicon-containing films. Low pressure chemical vapor deposition (LPCVD) using ammonia may require deposition temperatures of greater than 750° C. to obtain reasonable growth rates and uniformities. Higher deposition temperatures are typically employed to provide improved film properties. One of the more common industry methods to grow silicon nitride or other silicon-containing films is through low pressure chemical vapor deposition in a hot wall reactor at temperatures >750° C. using the precursors silane, dichlorosilane, and/or ammonia. However, there are several drawbacks using this method. For example, certain precursors, such as silane and dichlorosilane, are pyrophoric. This may present problems in handling and usage. Also, films deposited from silane and dichlorosilane may contain certain impurities. For example, films deposited using dichlorosilane may contain certain impurities, such as chlorine and ammonium chloride, which are formed as byproducts during the deposition process. Films deposited using silane may contain hydrogen.

Precursors that are used in depositing silicon nitride films such as BTBAS and chlorosilanes generally deposit the films at temperatures greater than 550° C. The trend of miniaturization of semiconductor devices and low thermal budget requires lower process temperature and higher deposition rate. The temperature, at which the silicon films are deposited, should decrease in order to prevent ion diffusion in the lattice, particularly for those substrates comprising metallization layers and on many Group III-V and II-VI devices. Accordingly, there is a need in the art to provide precursors for the deposition of silicon-containing films, such as silicon oxide or silicon nitride films that are sufficiently chemically reactive to allow deposition via CVD, ALD or other processes at temperatures of 550° C. or below or even at room temperature.

BRIEF SUMMARY OF THE INVENTION

Described herein are organoaminosilane precursors and methods using same for forming dielectric films comprising silicon, such as, but not limited to, silicon oxide, silicon nitride, silicon oxynitride, silicon carbide, silicon carbonitride, and combinations thereof onto at least a portion of a substrate. Also disclosed herein are the methods to forth dielectric films or coatings on an object to be processed, such as, for example, a semiconductor wafer. In one embodiment of the method described herein, a layer comprising silicon and oxygen is deposited onto a substrate using an organoaminosilane precursor and an oxidizing agent in a deposition chamber under conditions for generating a silicon oxide layer on the substrate. In another embodiment of the method described herein, a layer comprising silicon and nitrogen is deposited onto a substrate using an organoaminosilane precursor and a nitrogen containing precursor in a deposition chamber under conditions for generating a silicon nitride layer on the substrate. In a further embodiment, the organoaminosilane precursors described herein can also be used a dopant for metal containing films, such as but not limited to, metal oxide films or metal nitride films. In the processes described herein, an organoaminosilane having Formula I is employed as at least one of the silicon containing precursors.

In one aspect, the organoaminosilane precursor described herein comprises an organoaminosilane precursor represented by the following formula I:

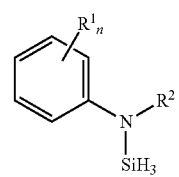

I wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a hydrogen atom, a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_6$ to $C_{10}$ aryl group, a $C_1$ to $C_6$ linear or branched fluorinated alkyl group, and a $C_4$ to $C_{10}$ cyclic alkyl group. In certain embodiments wherein n in formula I is a number greater than 1, $R^1$ is the same. In other embodiments wherein n in formula I is a number greater than 1, $R^1$ is different. In the foregoing or other embodiments, $R^1$ and $R^2$ can be linked together to form a ring. In the yet further embodiments, $R^1$ and $R^2$ are not linked together to form a ring.

In another aspect, there is provided a method for forming a silicon-containing film on at least one surface of a substrate comprising:

providing the at least one surface of the substrate in a reaction chamber; and forming the silicon-containing film on the at least one surface by a deposition process chosen from a chemical vapor deposition process and an atomic layer deposition process from an at least one organoaminosilane precursor represented by the following formula I:

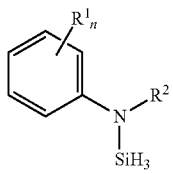

wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a hydrogen atom, a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_6$ to $C_{10}$ aryl group, a $C_1$ to $C_6$ linear or branched fluorinated alkyl group, and a $C_4$ to $C_{10}$ cyclic alkyl group. In one particular embodiment of Formula I, $R^1$ and $R^2$ can be linked together to form a ring. In another embodiment of Formula I, $R^1$ and $R^2$ are not linked together to form a ring.

In another aspect, there is provided a method of forming a silicon oxide film via an atomic layer deposition process, the method comprising the steps of:

a. providing a substrate in a reactor;

b. introducing into the reactor an at least one silicon precursor selected from an at least one organoaminosilane precursor represented by the following formula I:

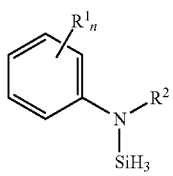

wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a hydrogen atom, a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_6$ to $C_{10}$ aryl group, a $C_1$ to $C_6$ linear or branched fluorinated alkyl group, and a $C_4$ to $C_{10}$ cyclic alkyl group;

c. purging the reactor with a purge gas;

d. introducing an oxygen source into the reactor;

e. purging the reactor with a purge gas; and f. repeating the steps b through e until a desired thickness of the film is obtained.

In a further aspect, there is provided a method of forming a silicon oxide film onto at least a surface of a substrate using a CVD process comprising:

a. providing a substrate in a reactor;

b. introducing into the reactor an at least one organoaminosilane precursor represented by the following formula I:

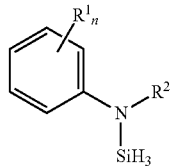

wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a hydrogen atom, a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_6$ to $C_{10}$ aryl group, a $C_1$ to $C_6$ linear or branched fluorinated alkyl group, and a $C_4$ to $C_{10}$ cyclic alkyl group; and c. providing an oxygen source to deposit the silicon oxide film onto the at least one surface.

In another aspect, there is provided a method of forming a silicon nitride film via an atomic layer deposition process, the method comprising the steps of:

a. providing a substrate in a reactor;

b. introducing into the reactor an at least one silicon precursor represented by the following formula I:

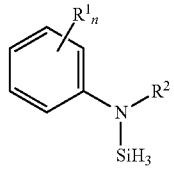

wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a hydrogen atom, a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_6$ to $C_{10}$ aryl group, a $C_1$ to $C_6$ linear or branched fluorinated alkyl group, and a $C_4$ to $C_{10}$ cyclic alkyl group;

c. purging the reactor with a purge gas;

d. introducing a nitrogen-containing source into the reactor;

e. purging the reactor with a purge gas; and f. repeating the steps b through e until a desired thickness of the silicon nitride film is obtained.

In a further aspect, there is provided a method of forming a silicon nitride film onto at least a surface of a substrate using a CVD process comprising:

a. providing a substrate in a reactor;

b. introducing into the reactor an at least one organoaminosilane precursor represented by the following formula I:

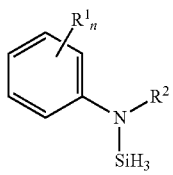

I wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a hydrogen atom, a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_6$ to $C_{10}$ aryl group, a $C_1$ to $C_6$ linear or branched fluorinated alkyl group, and a $C_4$ to $C_{10}$ cyclic alkyl group;

c. providing a nitrogen-containing source wherein the at least one organoaminosilane precursors and the nitrogen-containing source react to deposit the film comprising both silicon and nitrogen onto the at least one surface.

In another aspect, a vessel for depositing a dielectric film comprising one or more organoaminosilane precursor having Formula I is described herein. In one particular embodiment, the vessel comprises at least one pressurizable vessel (preferably of stainless steel) fitted with the proper valves and fittings to allow the delivery of one or more precursors to the reactor for a CVD or an ALD process.

BRIEF DESCRIPTION OF SEVERAL VIEWS OF THE DRAWINGS

FIG. 6 (C) provides a schematic view of the optimized hydroxylated $SiO_2$ (001) surface wherein O1 and O2 represent two types of surface hydroxyl groups.

DETAILED DESCRIPTION OF THE INVENTION

Figure 1:
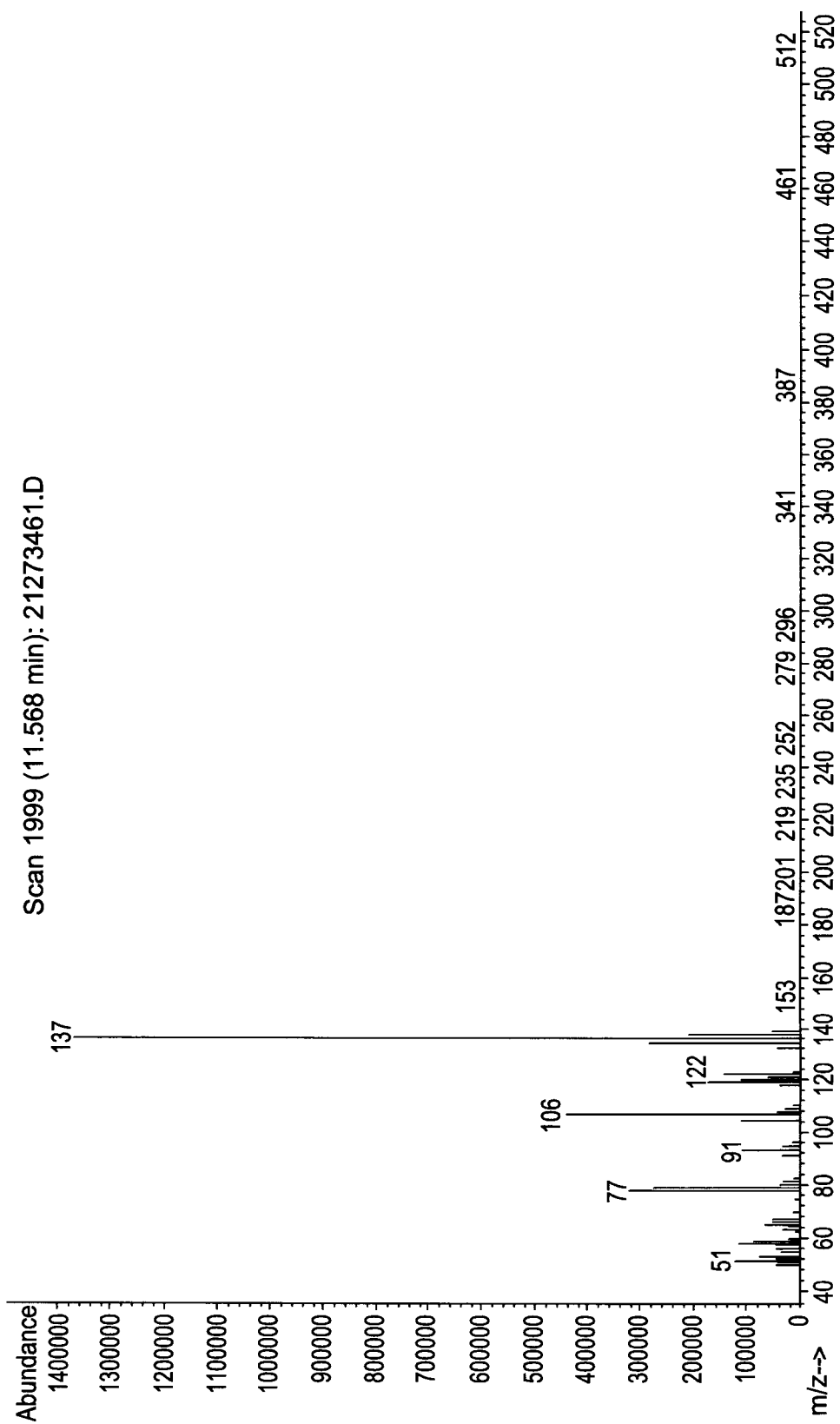
FIG. 1 provides the mass spectroscopy (MS) spectra of phenylmethylaminosilane of Example 1.

Organoaminosilanes, silane, or silicon-containing precursors are used as precursors to form stoichiometric and non-stoichiometric silicon containing films such as, but not limited to, silicon oxide, silicon oxycarbide, silicon nitride, silicon oxynitride and silicon oxycarbonitride. These precursors can also be used, for example, as dopants for metal containing films. The organoaminosilane precursors are typically high purity volatile liquid precursor chemical that are vaporized and delivered to a deposition chamber or reactor as a gas to deposit a silicon containing film via CVD or ALD processes for semiconductor devices. The selection of precursor materials for deposition depends upon the desired resultant dielectric material or film. For example, a precursor material may be chosen for its content of chemical elements, its stoichiometric ratios of the chemical elements, and/or the resultant dielectric film or coating that are formed under CVD. The precursor material may also be chosen for various other characteristics such as cost, non-toxicity, handling characteristics, ability to maintain liquid phase at room temperature, volatility, molecular weight, and/or other considerations. In certain embodiments, the precursors described herein can be delivered to the reactor system by any number of means, preferably using a pressurizable stainless steel vessel fitted with the proper valves and fittings, to allow the delivery of liquid phase precursor to the deposition chamber or reactor.

The organoaminosilanes precursors described herein exhibit a balance of reactivity and stability that makes them ideally suitable as CVD or ALD precursors. With regard to reactivity, certain precursors may have boiling points that are too high to be vaporized and delivered to the reactor to be deposited as a film on a substrate. Precursors having higher relative boiling points require that the delivery container and lines need to be heated at or above the boiling point of the precursor to prevent condensation or particles from forming in the container, lines, or both. With regard to stability, other precursors may form silane ($SiH_4$) as they degrade. Silane is pyrophoric at room temperature or it can spontaneously combust which presents safety and handling issues. Moreover, the formation of silane and other by-products decreases the purity level of the precursor and changes as small as 1-2% in chemical purity may be considered unacceptable for reliable semiconductor manufacture. In certain embodiments, the organoaminosilane precursors having formula I comprise less than 2% by weight, or less than 1% by weight, or less than 0.5% by weight of by-product (such as the corresponding bis-silane byproduct) after being stored for a 6 month or greater or one year or greater time period. In addition to the foregoing advantages, in certain embodiments such as for depositing a silicon oxide or silicon nitride film using an ALD or PEALD deposition method, the organoaminosilane precursor described herein may be able to deposit high density materials at relatively low deposition temperatures, e.g., at 500° C. or less, at 400° C. or less, or at 300° C. or less. In one particular embodiment, the organoaminosilane precursor, such as phenylmethylaminosilane, can be used to deposit a dielectric film via ALD or PEALD at a temperature as low as 50° C. or less or at room temperature (e.g., 25° C.).

In one aspect, there is provided certain precursors or organoaminosilanes that are represented by the following formula I:

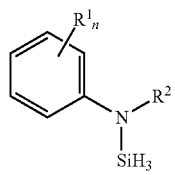

wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a hydrogen atom, a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_6$ to $C_{10}$ aryl group, a $C_1$ to $C_6$ linear or branched fluorinated alkyl group, and a $C_4$ to $C_{10}$ cyclic alkyl group. In certain embodiments of the organoaminosilane of Formula I, $R^1$ and $R^2$ can be linked together to form a ring. In alternative embodiments of the organoaminosilane of formula I, $R^1$ and $R^2$ are not linked together to form a ring.

In formula I and throughout the description, the term "alkyl" denotes a linear, or branched functional group having from 1 to 20 or 1 to 12 or 1 to 6 carbon atoms. Exemplary alkyl groups include, but are not limited to, methyl, ethyl, propyl, isopropyl, butyl, isobutyl, sec-butyl, tert-butyl, pentyl, isopentyl, tert-pentyl, hexyl, isohexyl, and neohexyl. In certain embodiments, the alkyl group may have one or more functional groups such as, but not limited to, an alkoxy group, a dialkylamino group or combinations thereof, attached thereto. In other embodiments, the alkyl group does not have one or more functional groups attached thereto.

In formula I and throughout the description, the term "cyclic alkyl" denotes a cyclic functional group having from 3 to 12 or from 4 to 10 carbon atoms. Exemplary cyclic alkyl groups include, but are not limited to, cyclobutyl, cyclopentyl, cyclohexyl, and cyclooctyl groups.

In formula I and throughout the description, the term "aryl" denotes an aromatic cyclic functional group having from 5 to 12 carbon atoms or from 6 to 10 carbon atoms. Exemplary aryl groups include, but are not limited to, phenyl, benzyl, chlorobenzyl, tolyl, and o-xylyl.

In formula I and throughout the description, the term "alkenyl group" denotes a group which has one or more carbon-carbon double bonds and has from 2 to 20 or from 2 to 12 or from 2 to 6 carbon atoms.

In formula I and throughout the description, the term "alkynyl group" denotes a group which has one or more carbon-carbon triple bonds and has from 2 to 20 or from 2 to 12 or from 2 to 6 carbon atoms.

In formula I and throughout the description, the term "alkoxy" denotes an alkyl group which has is linked to an oxygen atom (e.g., R—O) and may have from 1 to 20, or from 1 to 12, or from 1 to 6 carbon atoms. Exemplary alkoxy groups include, but are not limited to, methoxy (—$OCH_3$), ethoxy(—$OCH_2CH_3$), n-propoxy (—$OCH_2CH_2CH_3$), and iso-propoxy (—$OCHMe_2$).

In formula I and throughout the description, the term "dialkylamine group" denotes a group which has two alkyl groups attached to a nitrogen atom and has from 1 to 20 or from 2 to 12 or from 2 to 6 carbon atoms.

The term "electron withdrawing substituent" as used herein describes an atom or group thereof that acts to draw electrons away from the Si—N bond. Examples of suitable electron withdrawing substituents include, but are not limited to, halogens (F, Cl, Br, I) and nitriles (CN). In certain embodiments, electron withdrawing substituent can be adjacent to or proximal to N in formula I. Further non-limiting examples of an electron withdrawing group includes F, Cl, Br, I, CN, $NO_2$, RSO, and/or $RSO_2$ wherein R can be a $C_1$ to $C_{10}$ alkyl group such as, but not limited to, a methyl group or another group.

In certain embodiments, one or more of the alkyl group, alkenyl group, alkynyl group, alkoxy group, dialkylamino group, aryl group, and/or electron withdrawing group in formula I and II may be substituted or have one or more atoms or group of atoms substituted in place of, for example, a hydrogen atom. Exemplary substituents include, but are not limited to, oxygen, sulfur, halogen atoms (e.g., F, Cl, I, or Br), nitrogen, and phosphorous. In other embodiments, one or more of the alkyl group, alkenyl group, alkynyl group, alkoxy group, dialkylamino aryl group, and/or electron withdrawing group in Formula I and II may be unsubstituted.

In certain embodiments, substituents $R^1$ and $R^2$ are linked in formula I to form a ring structure. In other embodiments, substituent $R^1$ and $R^2$ are not linked in formula I.

In certain embodiments wherein n in formula I is a number greater than 1, $R^1$ is the same. An example of this can be an embodiment wherein n is 2 and the two $R_1$ substituents are both methyl groups. In other embodiments wherein n in formula I is a number greater than 1, $R^1$ is different. An example of this can be an embodiment wherein n is 2 and the two $R^1$ substituents are a methyl group and a Cl atom. In these or other embodiments, $R^1$ and $R^2$ are independent of each other. In alternative embodiments wherein n in formula I is a number greater than 1, one of substituents $R^1$ and $R^2$ are linked in formula I to form a ring structure.

In certain embodiments, the at least one organoaminosilane precursor having formula I has one or more substituents comprising oxygen atoms. In these embodiments, the need for an oxygen source during the deposition process may be avoided. In other embodiments, the at least one organoaminosilane precursor having formula I has one or more substituents comprising oxygen atoms also uses an oxygen source. In this or other embodiments, substituents $R^1$ and $R^2$ are linked via an oxygen atom in formula I to form a ring structure. The following Table 1 provides some non-limiting examples of certain embodiments of the organoaminosilanes having formula I.

TABLE 1

Exemplary Organoaminosilanes Having Formula I

| phenylmethylaminosilane (PMAS) | phenylethylaminosilane | phenyl-iso-propylaminosilane |
| --- | --- | --- |
| Phenylallylaminosilane | m-tolylmethylaminosilane | N-silyl-tetrahydroquinoline |
| N-silyl-3-anilinopropionitrile | N-silyl-N-phenylglycinonitrile | N-silylcarbazole |
| Phenylcyclohexylaminosilane | N-Silyl-2-methylindoline | N-silylbenzomorpholine |
| N-silylindole | N-silyl-2-methylindole | N-silyl-3-methylindole |
| o-tolylethylaminosilane | p-tolylethylaminosilane | m-tolylethylaminosilane |

TABLE 1-continued

Exemplary Organoaminosilanes Having Formula I

| p-tolylmethylaminosilane | o-tolylmethylaminosilane | N-silyl-1,2,3,4-Tetrahydro-2-methylquinoline |
|---|---|---|

Without being bound by theory, it is believed that organoaminosilane precursors such as those organoaminosilanes having formula I described herein and having a —SiH₃ group are advantageous over other organoaminosilane precursors containing SiH₂ or —SiH groups because of its lower activation barrier to react on a hydroxylated semi-conductor surface (thus lower deposition temperature), lower impurity and higher film density after deposition. However, certain organoaminosilane precursors having a —SiH₃ group such as dimethylaminosilane (DMAS) or diethylaminosilane (DEAS) may not be thermally stable because it undergoes a disproportionational reaction to form pyrophoric silane and bis(dimethylamino)silane or bis(diethylamino)silane, respectively. It has been found that the activation barrier for PMAS was relatively low compared with DMAS. Further, it is thought that films deposited using these particular organoaminosilane precursors may contain appropriate levels and types of carbon in silicon nitride or silicon carbonitride networks that may enable a significant reduction in wet etch rate yet maintaining a certain dielectric constant value. In addition, it has also been found that the present organoaminosilane precursors having Formula I described herein may allow for lower temperature depositions, such as, for example, room temperature depositions, than other organoaminosilanes known in the art such as diisopropylaminosilane.

In certain embodiments, the organoaminosilanes having formula I can be prepared by reacting a monochlorosilane (MCS) or lower molecular dialkylaminosilane such as di-iso-propylaminosilane with an amine having the following Formula II in an organic solvent or solvent mixture.

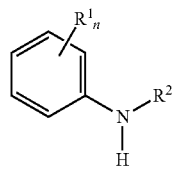

II

In formula II, substituent $R^1$ in formula II is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a hydrogen atom, a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_6$ to $C_{10}$ aryl group, a linear or branched $C_1$ to $C_6$ fluorinated alkyl group, and a $C_4$ to $C_{10}$ cyclic alkyl group. In one embodiment of the amine having formula II, $R^1$ and $R^2$ can be linked together to form a ring. In an alternative embodiment of the amine having formula II, $R^1$ and $R^2$ are not linked together to form a ring. Exemplary amines having formula II wherein $R^1$ is hydrogen, a linear or branched $C_1$ to $C_6$ alkyl group, halide and $R^2$ is a linear or branched $C_1$ to $C_6$ alkyl group or a $C_4$ to $C_{10}$ cyclic alkyl include, but are not limited to, N-methylaniline, N-ethylaniline, N-iso-propylaniline, n-Butylaniline, N-allylaniline, N-Ethyl-m-toluidine, N-Methyl-o-toluidine, N-Methyl-p-toluidine, 4-fluoro-N-methylaniline, 4-Chloro-N-methylaniline, N-cyclohexylaniline, 3-anilinopropionitrile, or N-phenylglycinonitrile. Exemplary amines having formula II wherein $R^1$ and $R^2$ are linked to form a ring include, but are not limited to, 3-methylindole, 2-methylindole, indole, tetrahydroquinoline, 8-methyl-1,2,3,4-tetrahydroquinoline, 3-indoleacetonitrile, 2-methylindoline, 2,3-dihydroindole, 5-methylindoline, 1,2,3,4-tetrahydroquinoline, 1,2,3,4-tetrahydro-2-methylquinoline, 1,2,3,4-tetrahydro-6-methylquinoline, 3,4-dihydro-2H-1,4-benzoxazine, carbazole, and 3,6-dibromocarbazole.

The following Equations 1 through 3 provide examples of reaction schemes or synthesis routes which may be used to make the organoaminosilanes having formula I as described herein. Reaction schemes 1 through 3 can be conducted with (e.g., in the presence of) or without (e.g., in the absence of) organic solvents. In embodiments wherein an organic solvent is used, examples of suitable organic solvents include, but are not limited to, hydrocarbon such as hexanes, octane, toluene, and ethers such as diethylether, and tetrahydrofuran (THF). In these or other embodiments, the reaction temperature is in the range of from about −70° C. to the boiling point of the solvent employed if a solvent is involved. The resulting organoaminosilane can be purified via vacuum distillation after removing all by-products as well as solvent(s) if present. Equation 1 is an embodiment involving a silyl exchange reaction. An example of this synthetic route is provided herein as Example 1. Equation 2 is an embodiment wherein a chlorinated silane is used as a reagent. An example of this synthetic route is provided herein as Example 2. Equation 3 is an embodiment wherein a metal amide such as a lithium or potassium amide and a chlorinated silane are used as reagents and results in the desired end product and a metal halide by-product.

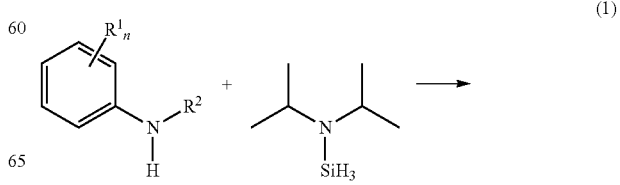

(1)

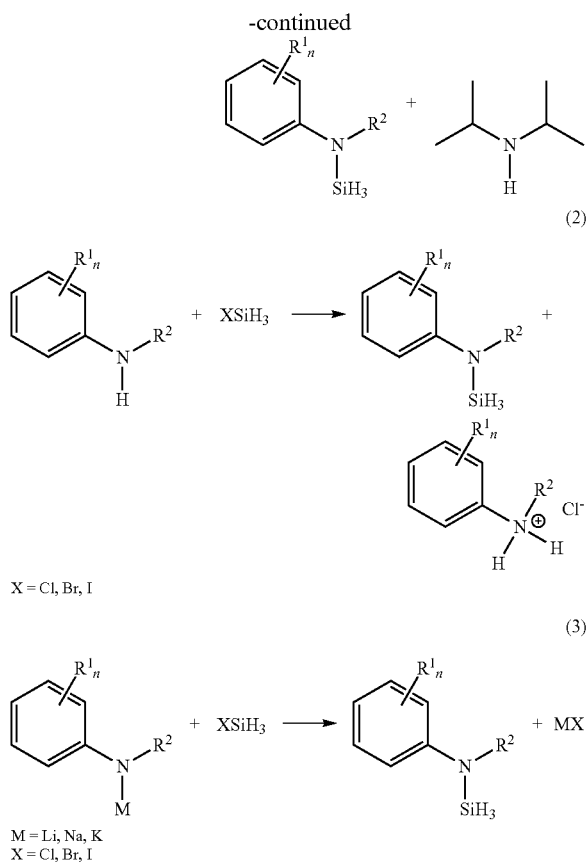

The method used to form the silicon-containing dielectric films or coatings are deposition processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition ("PECVD"), high density PECVD, photon assisted CVD, plasma-photon assisted ("PPECVD"), cryogenic chemical vapor deposition, chemical assisted vapor deposition, hot-filament chemical vapor deposition, CVD of a liquid polymer precursor, deposition from supercritical fluids, and low energy CVD (LECVD). In certain embodiments, the metal containing films are deposited via atomic layer deposition (ALD), plasma enhanced ALD (PEALD) or plasma enhanced cyclic CVD (PECCVD) process. As used herein, the term "chemical vapor deposition processes" refers to any process wherein a substrate is exposed to one or more volatile precursors, which react and/or decompose on the substrate surface to produce the desired deposition. As used herein, the term "atomic layer deposition process" refers to a self-limiting (e.g., the amount of film material deposited in each reaction cycle is constant), sequential surface chemistry that deposits films of materials onto substrates of varying compositions. Although the precursors, reagents and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator. In one embodiment, the dielectric film is deposited using an ALD process. In another embodiment, the dielectric film is deposited using a CCVD process. In a further embodiment, the dielectric film is deposited using a thermal CVD process.

The term "reactor" as used herein, includes without limitation, reaction chamber or deposition chamber.

In certain embodiments, the method disclosed herein avoids pre-reaction of the precursors by using ALD or CCVD methods that separate the precursors prior to and/or during the introduction to the reactor. In this connection, deposition techniques such as ALD or CCVD processes are used to deposit the dielectric film. In one embodiment, the film is deposited via an ALD process by exposing the substrate surface alternatively to the one or more the silicon-containing precursor, oxygen source, nitrogen-containing source, or other precursor or reagent. Film growth proceeds by self-limiting control of surface reaction, the pulse length of each precursor or reagent, and the deposition temperature. However, once the surface of the substrate is saturated, the film growth ceases.

In certain embodiments, the method described herein further comprises one or more additional silicon-containing precursors other than the organoaminosilane precursor having the above formula I. Examples of additional silicon-containing precursors include, but are not limited to, organo-silicon compounds such as siloxanes (e.g., hexamethyl disiloxane (HMDSO) and dimethyl siloxane (DMSO)); organosilanes (e.g., methylsilane; dimethylsilane; vinyl trimethylsilane; trimethylsilane; tetramethylsilane; ethylsilane; disilylmethane; 2,4-disilapentane; 1,4-disilabutane; 2,5-disilahexane; 2,2-disilylpropane; 1,3,5-trisilacyclohexane, and fluorinated derivatives of these compounds; phenyl-containing organo-silicon compounds (e.g., dimethylphenylsilane and diphenylmethylsilane); oxygen-containing organo-silicon compounds, e.g., dimethyldimethoxysilane; 1,3,5,7-tetramethylcyclotetrasiloxane; 1,1,3,3-tetramethyldisiloxane; 1,3,5,7-tetrasila-4-oxo-heptane; 2,4,6,8-tetrasila-3,7-dioxo-nonane; 2,2-dimethyl-2,4,6,8-tetrasila-3,7-dioxo-nonane; octamethylcyclotetrasiloxane; [1,3,5,7,9]-pentamethylcyclopentasiloxane; 1,3,5,7-tetrasila-2,6-dioxo-cyclooctane; hexamethylcyclotrisiloxane; 1,3-dimethyldisiloxane; 1,3,5,7,9-pentamethylcyclopentasiloxane; hexamethoxydisiloxane, and fluorinated derivatives of these compounds.

Depending upon the deposition method, in certain embodiments, the one or more silicon-containing precursors may be introduced into the reactor at a predetermined molar volume, or from about 0.1 to about 1000 micromoles. In this or other embodiments, the silicon-containing and/or organoaminosilane precursor may be introduced into the reactor for a predetermined time period. In certain embodiments, the time period ranges from about 0.001 to about 500 seconds.

In certain embodiments, the dielectric films deposited using the methods described herein are formed in the presence of oxygen using an oxygen source, reagent or precursor comprising oxygen. An oxygen source may be introduced into the reactor in the form of at least one oxygen source and/or may be present incidentally in the other precursors used in the deposition process. Suitable oxygen source gases may include, for example, water ($H_2O$) (e.g., deionized water, purifier water, and/or distilled water), oxygen ($O_2$), oxygen plasma, ozone ($O_3$), NO, $NO_2$, carbon monoxide (CO), carbon dioxide ($CO_2$) and combinations thereof. In certain embodiments, the oxygen source comprises an oxygen source gas that is introduced into the reactor at a flow rate ranging from about 1 to about 2000 square cubic centimeters (sccm) or from about 1 to about 1000 sccm. The oxygen source can be introduced for a time that ranges from about 0.1 to about 100 seconds. In one particular embodiment, the oxygen source comprises water having a temperature of 10° C. or greater. In embodiments wherein the film is deposited by an ALD or a cyclic CVD process, the precursor pulse can have a pulse duration that is greater than 0.01 seconds, and the oxygen source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between. The oxygen source or reagent is provided in a molecular amount less than a 1:1 ratio to the silicon precursor, so that at least some carbon is retained in the as deposited dielectric film.

In certain embodiments, the dielectric films comprise silicon and nitrogen. In these embodiments, the dielectric films deposited using the methods described herein are formed in the presence of nitrogen-containing source. An nitrogen-containing source may be introduced into the reactor in the form of at least one nitrogen source and/or may be present incidentally in the other precursors used in the deposition process. Suitable nitrogen-containing source gases may include, for example, ammonia, hydrazine, monoalkylhydrazine, dialkylhydrazine, nitrogen, nitrogen/hydrogen, ammonia plasma, nitrogen plasma, nitrogen/hydrogen plasma, and mixture thereof. In certain embodiments, the nitrogen-containing source comprises an ammonia plasma or hydrogen/nitrogen plasma source gas that is introduced into the reactor at a flow rate ranging from about 1 to about 2000 square cubic centimeters (sccm) or from about 1 to about 1000 sccm. The nitrogen-containing source can be introduced for a time that ranges from about 0.1 to about 100 seconds. In embodiments wherein the film is deposited by an ALD or a cyclic CVD process, the precursor pulse can have a pulse duration that is greater than 0.01 seconds, and the nitrogen-containing source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between.

The deposition methods disclosed herein may involve one or more purge gases. The purge gas, which is used to purge away unconsumed reactants and/or reaction byproducts, is an inert gas that does not react with the precursors. Exemplary purge gases include, but are not limited to, argon (Ar), nitrogen ($N_2$), helium (He), neon, hydrogen ($H_2$), and mixtures thereof. In certain embodiments, a purge gas such as Ar is supplied into the reactor at a flow rate ranging from about 10 to about 2000 sccm for about 0.1 to 1000 seconds, thereby purging the unreacted material and any byproduct that may remain in the reactor.

The respective step of supplying the precursors, oxygen source, the nitrogen-containing source, and/or other precursors, source gases, and/or reagents may be performed by changing the time for supplying them to change the stoichiometric composition of the resulting dielectric film.

Energy is applied to the at least one of the precursor, nitrogen-containing source, reducing agent, other precursors or combination thereof to induce reaction and to form the dielectric film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

The organoaminosilane precursors and/or other silicon-containing precursors may be delivered to the reaction chamber such as a CVD or ALD reactor in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, which leads to reproducible transport and deposition without thermal decomposition of the precursor. In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

In another embodiment, a vessel for depositing a dielectric film comprising one or more organoaminosilane precursor having formula I is described herein. In one particular embodiment, the vessel comprises at least one pressurizable vessel (preferably of stainless steel) fitted with the proper valves and fittings to allow the delivery of one or more precursors to the reactor for a CVD or an ALD process. In this or other embodiments, the organoaminosilane precursor of Formula I is provided in a pressurizable vessel comprised of stainless steel and the purity of the precursor is 98% by weight or greater or 99.5% or greater which is suitable for the majority of semiconductor applications. In certain embodiments, such vessels can also have means for mixing the precursors with one or more additional precursor if desired. In these or other embodiments, the contents of the vessel(s) can be premixed with an additional precursor. Alternatively, the organoaminosilane precursor and/or other precursor can be maintained in separate vessels or in a single vessel having separation means for maintaining the organoaminosilane precursor and other precursor separate during storage.

In one embodiment of the method described herein, a cyclic deposition process such as CCVD, ALD, or PEALD may be employed, wherein at least one silicon-containing precursor selected from an organoaminosilane precursor having Formula I and optionally a nitrogen-containing source such as, for example, ammonia, hydrazine, monoalkylhydrazine, dialkylhydrazine, nitrogen, nitrogen/hydrogen, ammonia plasma, nitrogen plasma, nitrogen/hydrogen plasma are employed.

In certain embodiments, the gas lines connecting from the precursor canisters to the reaction chamber are heated to one or more temperatures depending upon the process requirements and the container of the organoaminosilane precursor having Formula I is kept at one or more temperatures for bubbling. In other embodiments, a solution comprising the at least one silicon-containing precursor having Formula I is injected into a vaporizer kept at one or more temperatures for direct liquid injection.

A flow of argon and/or other gas may be employed as a carrier gas to help deliver the vapor of the at least one organoaminosilane precursor to the reaction chamber during the precursor pulsing. In certain embodiments, the reaction chamber process pressure is about 1 Torr.

In a typical ALD or CCVD process, the substrate such as a silicon oxide substrate is heated on a heater stage in a reaction chamber that is exposed to the silicon-containing precursor initially to allow the complex to chemically adsorb onto the surface of the substrate.

A purge gas such as argon purges away unabsorbed excess complex from the process chamber. After sufficient purging, a nitrogen-containing source may be introduced into reaction chamber to react with the absorbed surface followed by another gas purge to remove reaction by-products from the chamber. The process cycle can be repeated to achieve the desired film thickness.

In this or other embodiments, it is understood that the steps of the methods described herein may be performed in a variety of orders, may be performed sequentially or concurrently (e.g., during at least a portion of another step), and any combination thereof. The respective step of supplying the precursors and the nitrogen-containing source gases may be performed by varying the duration of the time for supplying them to change the stoichiometric composition of the resulting dielectric film.

In another embodiment of the method disclosed herein, the films containing both silicon and nitrogen are formed using a ALD deposition method that comprises the steps of:

providing a substrate in an ALD reactor;

introducing into the ALD reactor an at least one organoaminosilane precursor comprising a precursor represented by the following formula I:

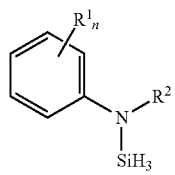

wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a hydrogen atom, a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_6$ to $C_{10}$ aryl group, a linear or branched $C_1$ to $C_6$ fluorinated alkyl group, and a $C_4$ to $C_{10}$ cyclic alkyl group;

chemisorbing the at least one organoaminosilane precursor onto a substrate;

purging away the unreacted at least one organoaminosilane precursor using a purge gas;

providing a nitrogen-containing source to the organoaminosilane precursor onto the heated substrate to react with the sorbed at least one organoaminosilane precursor; and optionally purging away any unreacted nitrogen-containing source.

In another embodiment of the method disclosed herein, the dielectric films is formed using a ALD deposition method that comprises the steps of:

providing a substrate in a reactor;

introducing into the reactor an at least one organoaminosilane precursor represented by the following formula I:

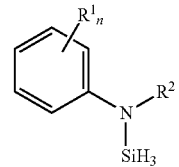

wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a hydrogen atom, a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_6$ to $C_{10}$ aryl group, a linear or branched $C_1$ to $C_6$ fluorinated alkyl group, and a $C_4$ to $C_{10}$ cyclic alkyl group;

chemisorbing the at least one organoaminosilane precursor onto a substrate;

purging away the unreacted at least one organoaminosilane precursor using a purge gas;

providing an oxygen source to the organoaminosilane precursor onto the heated substrate to react with the sorbed at least one organoaminosilane precursor; and optionally purging away any unreacted oxygen source.

The above steps define one cycle for the method described herein; and the cycle can be repeated until the desired thickness of a dielectric film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen source may be performed by varying the duration of the time for supplying them to change the stoichiometric composition of the resulting dielectric film, although always using oxygen in less than a stoichiometric amount relative to the available silicon.

For multi-component dielectric films, other precursors such as silicon-containing precursors, nitrogen-containing precursors, reducing agents, or other reagents can be alternately introduced into the reactor chamber.

In a further embodiment of the method described herein, the dielectric film is deposited using a thermal CVD process. In this embodiment, the method comprises:

placing one or more substrates into a reactor which is heated to a temperature ranging from ambient temperature to about 700° C. and maintained at a pressure of 1 Torr or less;

introducing at least one organoaminosilane precursor having the following formula I:

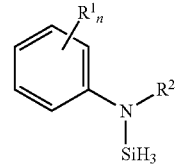

wherein R¹ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and R² is independently selected from a hydrogen atom, a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_6$ to $C_{10}$ aryl group, a linear or branched $C_1$ to $C_6$ fluorinated alkyl group, and a $C_4$ to $C_{10}$ cyclic alkyl group; and providing an oxygen source into the reactor to at least partially react with the at least one organoaminosilane precursor and deposit a dielectric film onto the one or more substrates. In certain embodiments of the CVD method, the reactor is maintained at a pressure ranging from 100 mTorr to 600 mTorr during the introducing step.

The above steps define one cycle for the method described herein; and the cycle can be repeated until the desired thickness of a dielectric film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen source may be performed by varying the duration of the time for supplying them to change the stoichiometric composition of the resulting dielectric film, although always using oxygen in less than a stoichiometric amount relative to the available silicon.

For multi-component dielectric films, other precursors such as silicon-containing precursors, nitrogen-containing precursors, oxygen sources, reducing agents, and/or other reagents can be alternately introduced into the reactor chamber.

In a further embodiment of the method described herein, the dielectric film is deposited using a thermal CVD process. In this embodiment, the method comprises:

placing one or more substrates into a reactor which is heated to a temperature ranging from ambient temperature to about 700° C. and maintained at a pressure of 1 Torr or less;

introducing at least one organoaminosilane precursor having the following formula I:

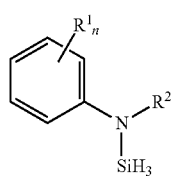

I wherein R¹ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and R² is independently selected from a hydrogen atom, a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_6$ to $C_{10}$ aryl group, a linear or branched $C_1$ to $C_6$ fluorinated alkyl group, and a $C_4$ to $C_{10}$ cyclic alkyl group; and providing a nitrogen-containing source into the reactor to at least partially react with the at least one organoaminosilane precursor and deposit a dielectric film onto the one or more substrates. In certain embodiments of the CVD method, the reactor is maintained at a pressure ranging from 100 mTorr to 600 mTorr during the introducing step.

In certain embodiments, the organoaminosilane precursors having Formula I described herein can also be used a dopant for metal containing films, such as but not limited to, metal oxide films or metal nitride films. In these embodiments, the metal containing film is deposited using an ALD or CVD process such as those processes described herein using metal alkoxide, metal amide, or volatile organometallic precursors. Examples of suitable metal alkoxide precursors that may be used with the method disclosed herein include, but are not limited to, group 3 to 6 metal alkoxide, group 3 to 6 metal complexes having both alkoxy and alkyl substituted cyclopentadienyl ligands, group 3 to 6 metal complexes having both alkoxy and alkyl substituted pyrrolyl ligands, group 3 to 6 metal complexes having both alkoxy and diketonate ligands; group 3 to 6 metal complexes having both alkoxy and ketoester ligands; Examples of suitable metal amide precursors that may be used with the method disclosed herein include, but are not limited to, tetrakis(dimethylamino)zirconium (TDMAZ), tetrakis(diethylamino)zirconium (TDEAZ), tetrakis(ethylmethylamino)zirconium (TEMAZ), tetrakis(dimethylamino)hafnium (TDMAH), tetrakis(diethylamino)hafnium (TDEAH), and tetrakis(ethylmethylamino) hafnium (TEMAH), tetrakis(dimethylamino)titanium (TDMAT), tetrakis(diethylamino)titanium (TDEAT), tetrakis(ethylmethylamino)titanium (TEMAT), tert-butylimino tri(diethylamino)tantalum (TBTDET), tert-butylimino tri(dimethylamino)tantalum (TBTDMT), tert-butylimino tri(ethylmethylamino)tantalum (TBTEMT), ethylimino tri(diethylamino)tantalum (EITDET), ethylimino tri(dimethylamino)tantalum (EITDMT), ethylimino tri(ethylmethylamino)tantalum (EITEMT), tert-amylimino tri(dimethylamino)tantalum (TAIMAT), tert-amylimino tri(diethylamino)tantalum, pentakis(dimethylamino)tantalum, tert-amylimino tri(ethylmethylamino)tantalum, bis(tert-butylimino)bis(dimethylamino)tungsten (BTBMW), bis(tert-butylimino)bis(diethylamino)tungsten, bis(tert-butylimino) bis(ethylmethylamino)tungsten, and combinations thereof. Examples of suitable organometallic precursors that may be used with the method disclosed herein include, but are not limited to, group 3 metal cyclopentadienyls or alkyl cyclopentadienyls. Exemplary Group 3 to 6 metal herein include, but not limited to, Y, La, Ce, Pr, Nd, Sm, Eu, Gd, Tb, Dy, Er, Yb, Lu, Ti, Hf, Zr, V, Nb, Ta, Cr, Mo, and W.

In certain embodiments, the resultant dielectric films or coatings can be exposed to a post-deposition treatment such as, but not limited to, a plasma treatment, chemical treatment, ultraviolet light exposure, electron beam exposure, and/or other treatments to affect one or more properties of the film.

In certain embodiments, the dielectric films described herein have a dielectric constant of 6 or less. In these or other embodiments, the films can a dielectric constant of about 5 or below, or about 4 or below, or about 3.5 or below. However, it is envisioned that films having other dielectric constants (e.g., higher or lower) can be formed depending upon the desired end-use of the film. An example of the silicon containing or dielectric film that is formed using the organoaminosilane precursors and processes described herein has the formulation $Si_xO_yC_zN_vH_w$ wherein Si ranges from about 10% to about 40%; O ranges from about 0% to about 65%; C ranges from about 0% to about 75% or from about 0% to about 50%; N ranges from about 0% to about 75% or from about 0% to 50%; and H ranges from about 0% to about 50% atomic percent weight % wherein x+y+z+v+w=100 atomic weight percent, as determined for example, by XPS or other means.

As mentioned previously, the method described herein may be used to deposit a silicon-containing film on at least a portion of a substrate. Examples of suitable substrates include but are not limited to, silicon, $SiO_2$, $Si_3N_4$, OSG, FSG, silicon carbide, hydrogenated silicon carbide, silicon nitride, hydrogenated silicon nitride, silicon carbonitride, hydrogenated silicon carbonitride, boronitride, antireflective coatings, photoresists, organic polymers, porous organic and inorganic materials, metals such as copper and aluminum, and diffusion barrier layers such as but not limited to TiN, Ti(C)N, TaN, Ta(C)N, Ta, W, or WN. The films are compatible with a variety of subsequent processing steps such as, for example, chemical mechanical planarization (CMP) and anisotropic etching processes.

The deposited films have applications, which include, but are not limited to, computer chips, optical devices, magnetic information storages, coatings on a supporting material or substrate, microelectromechanical systems (MEMS), nanoelectromechanical systems, thin film transistor (TFT), and liquid crystal displays (LCD).

The following examples illustrate the method for preparing organoaminosilane precursors as well as deposited silicon-containing films described herein and are not intended to limit it in any way.

EXAMPLES

In the following examples, unless stated otherwise, properties were obtained from sample films that were deposited onto medium resistivity (8-12 Ωcm) single crystal silicon wafer substrates.

Example 1

Synthesis of Phenylmethylaminosilane Using Silyl Exchange Reaction

In a 500 ml Schlenk flask, 64.2 grams (g) (0.6 mol) N-methylaniline and 131 g (1.0 mol) di-isopropylaminosilane were stirred at ambient temperature under a nitrogen atmosphere for 24 hours. The relatively lower boiling point by-product di-isopropylamine was removed with vacuum at a pressure of 20 mmHg and room temperature (25° C.). The reaction mixture was stirred for another 24 hours. The end-product phenylmethylaminosilane (73.6 g, 89.5% yield) was obtained by vacuum distillation with a boiling point of 60° C. at 5 mm Hg. The end-product was characterized by mass spectroscopy (MS) which is provided in FIG. 1 and shows, among other things, peaks at 137, 122, 106, 91, and 77. The molecular weight of the phenylmethylaminosilane was 137.27.

Example 2

Alternative Synthesis Method for Phenylmethylaminosilane Using Monochloroaminosilane as a Reagent In a 2000 ml three-necked flask equipped with a mechanical stirrer, a condenser, and a gas bubbling inlet, 1000 ml hexane, 53.5 g (0.5 mol) N-methylaniline, and 50.5 g (0.5 mol) triethylamine were cooled to −20° C. with stirring under nitrogen atmosphere. Monochlorosilane (MCS) was bubbled through the reaction mixture. A white solid precipitate was formed. After the reaction was complete, the temperature of the reaction mixture was allowed to warm to room temperature while stirring continued for an additional 2 hours at room temperature. Solid triethylamine hydrochloride salt was removed by filtration, and the solvent hexane was removed by distillation. The product phenylmethylaminosilane (51.3 g, 75% yield) was obtained by vacuum distillation with boiling point of 60 C at 5 mm Hg. The compound was characterized by mass spectroscopy and confirms that the product is phenylmethylaminosilane. A comparison of Examples 1 and 2 shows that the synthesis method of Example 1 provided a higher product yield and is more convenient in lab scale synthesis.

Example 3

Synthesis of Phenylethylaminosilane Using Silyl Exchange Reaction

Figure 2:
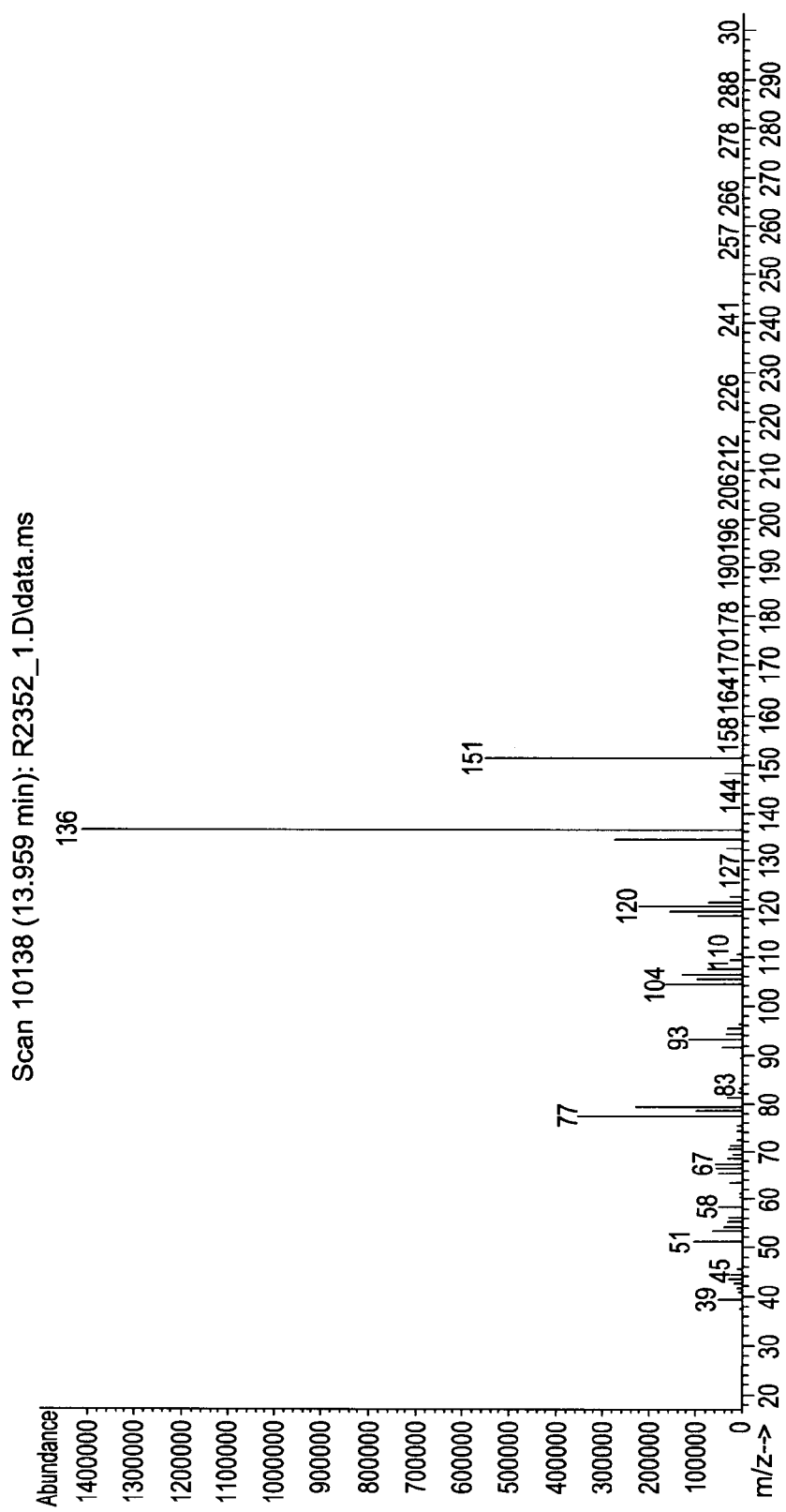
FIG. 2 provides the mass spectroscopy (MS) spectra of phenylethylaminosilane of Example 3.

In a 500 ml Schlenk flask, 60.5 g (0.5 mol) N-ethylaniline and 131 g (1.0 mol) di-isopropylaminosilane were stirred at ambient temperature under a nitrogen atmosphere for 24 hours. The relatively lower boiling point by-product di-isopropylamine was removed with vacuum at a pressure of 20 mmHg and room temperature (25° C.). The reaction mixture was stirred for another 24 hours. The end-product phenylethylaminosilane was obtained by vacuum distillation. The end-product was characterized by mass spectroscopy (MS) which is provided in FIG. 2 and shows, among other things, peaks at 151, 150, 136, 120, 106, 93, and 77. The molecular weight of the phenylethylaminosilane was 151.28.

Example 4

Synthesis of Phenylallylaminosilane Using Silyl Exchange Reaction

Figure 3:
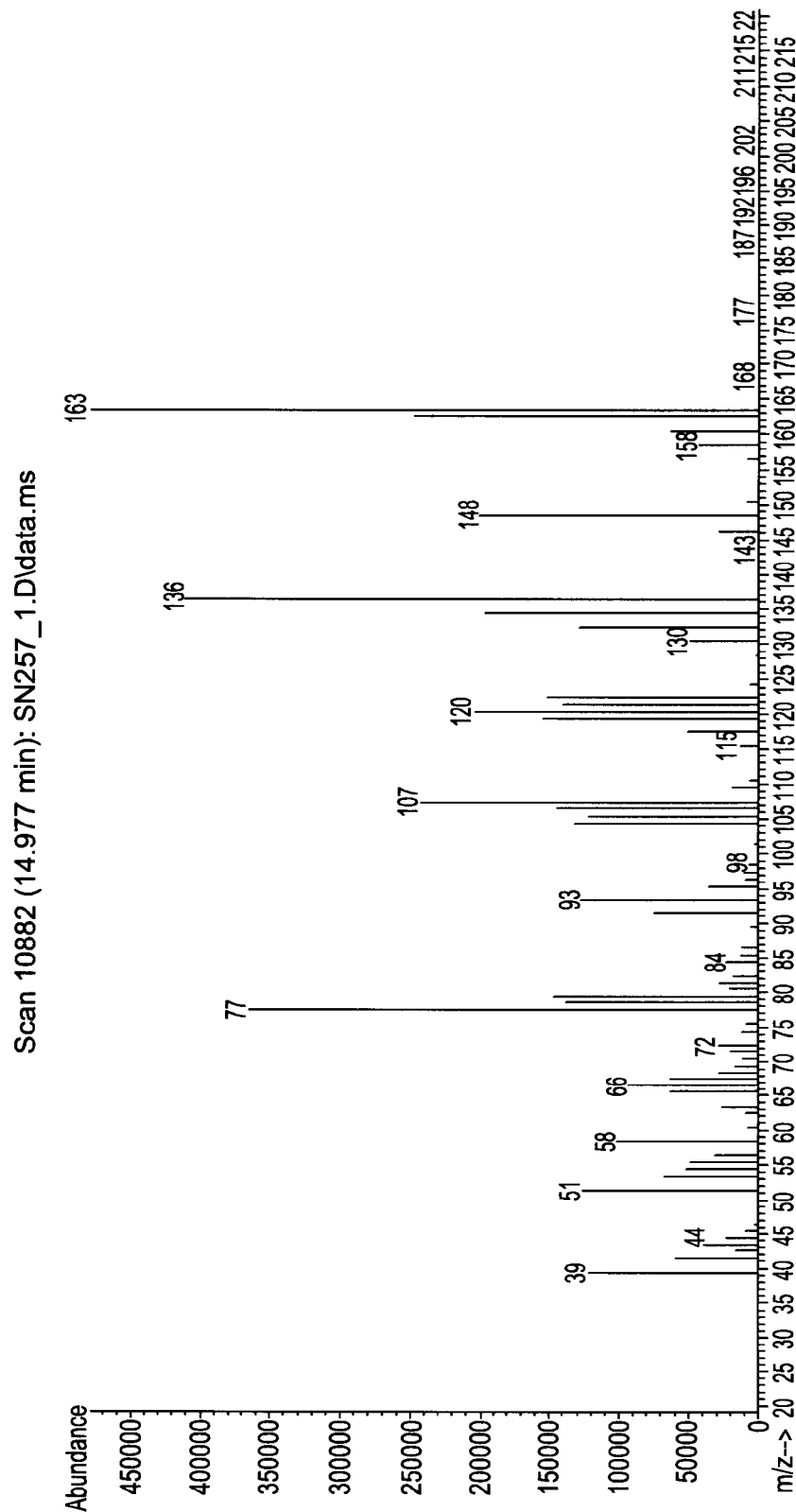
FIG. 3 provides the mass spectroscopy (MS) spectra of phenylallylaminosilane of Example 4.

In a 500 ml Schlenk flask, 62.5 g (0.5 mol) N-allylaniline and 131 g (1.0 mol) di-isopropylaminosilane were stirred at ambient temperature under a nitrogen atmosphere for 24 hours. The relatively lower boiling point by-product di-isopropylamine was removed with vacuum at a pressure of 20 mmHg and room temperature (25° C.). The reaction mixture was stirred for another 24 hours. The end-product phenylallylaminosilane was obtained by vacuum distillation. The end-product was characterized by mass spectroscopy (MS) which is provided in FIG. 3 and shows, among other things, peaks at 163, 162, 148, 136, 120, 107, 93, and 77. The molecular weight of the phenylallylaminosilane was 163.29.

Example 5

Synthesis of N-silyl-2-methylindoline Using Silyl Exchange Reaction

Figure 4:
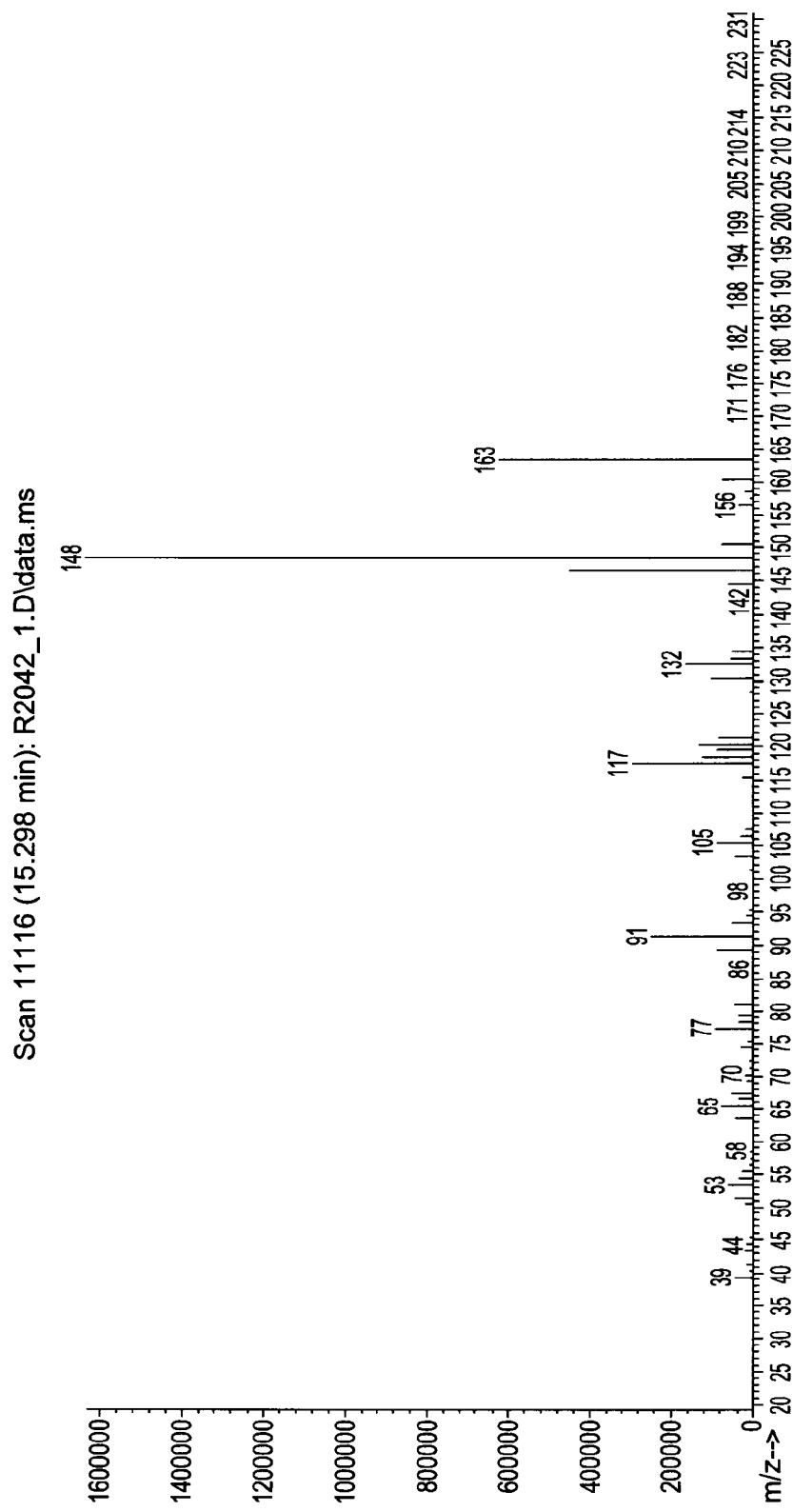
FIG. 4 provides the mass spectroscopy (MS) spectra of N-silyl-2-methylindoline of Example 5.

In a 500 ml Schlenk flask, 62.5 g (0.5 mol) 2-methylindoline and 131 g (1.0 mol) di-isopropylaminosilane were stirred at ambient temperature under a nitrogen atmosphere for 24 hours. The relatively lower boiling point by-product di-isopropylamine was removed with vacuum at a pressure of 20 mmHg and room temperature (25° C.). The reaction mixture was stirred for another 24 hours. The end-product N-silyl-2-methylindoline was obtained by vacuum distillation. The compound was characterized by mass spectroscopy (MS). The end-product was characterized by mass spectroscopy (MS) which is provided in FIG. 4 and shows, among other things, peaks at 163, 162, 148, 132, 117, 105, 91, and 77. The molecular weight of the N-silyl-2-methylindoline was 163.29.

Example 6

Synthesis of Phenylcyclohexylaminosilane Using Silyl Exchange Reaction

Figure 5:
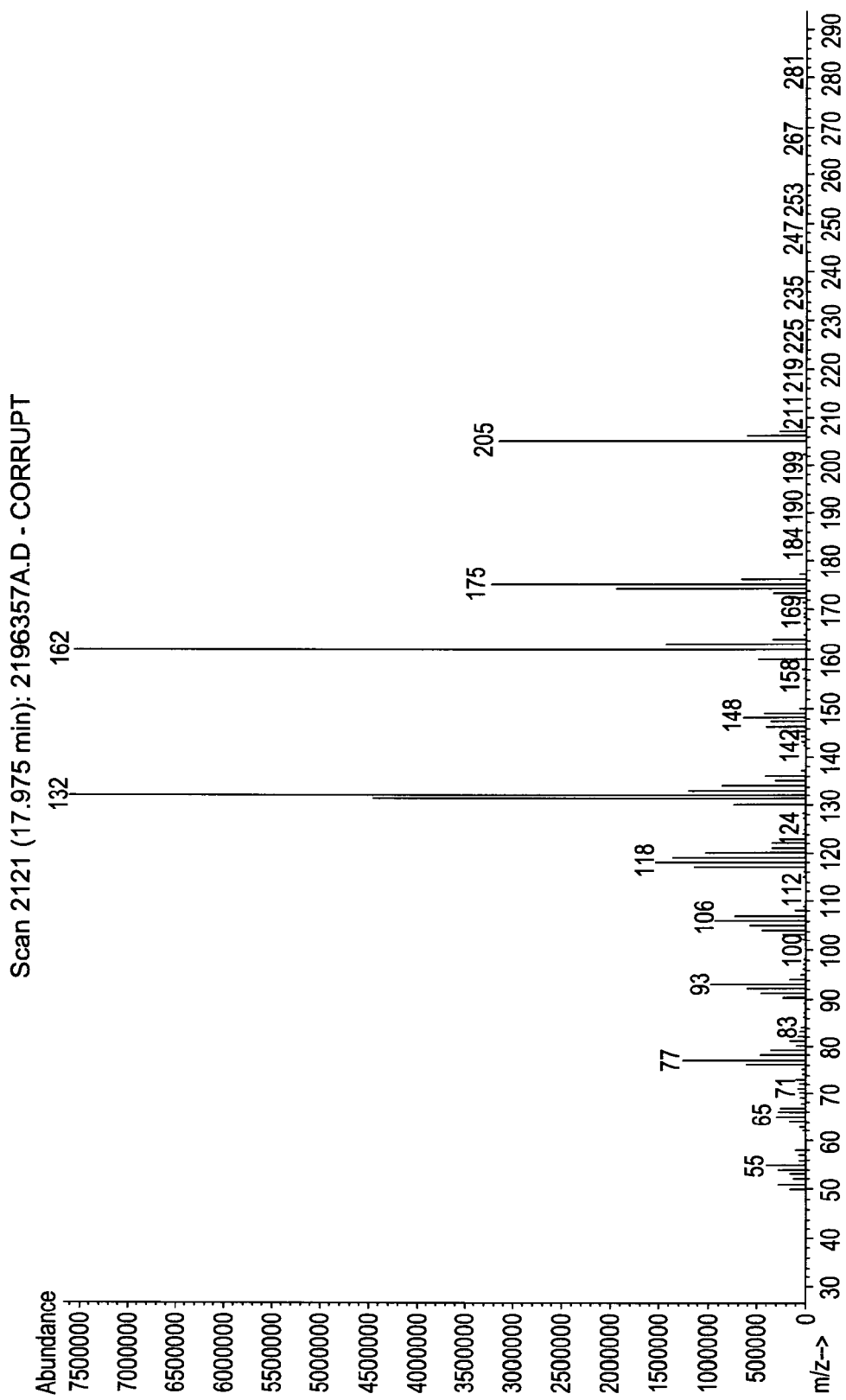
FIG. 5 provides the mass spectroscopy (MS) spectra of phenylcyclohexylaminosilane of Example 6.
Figure 6:
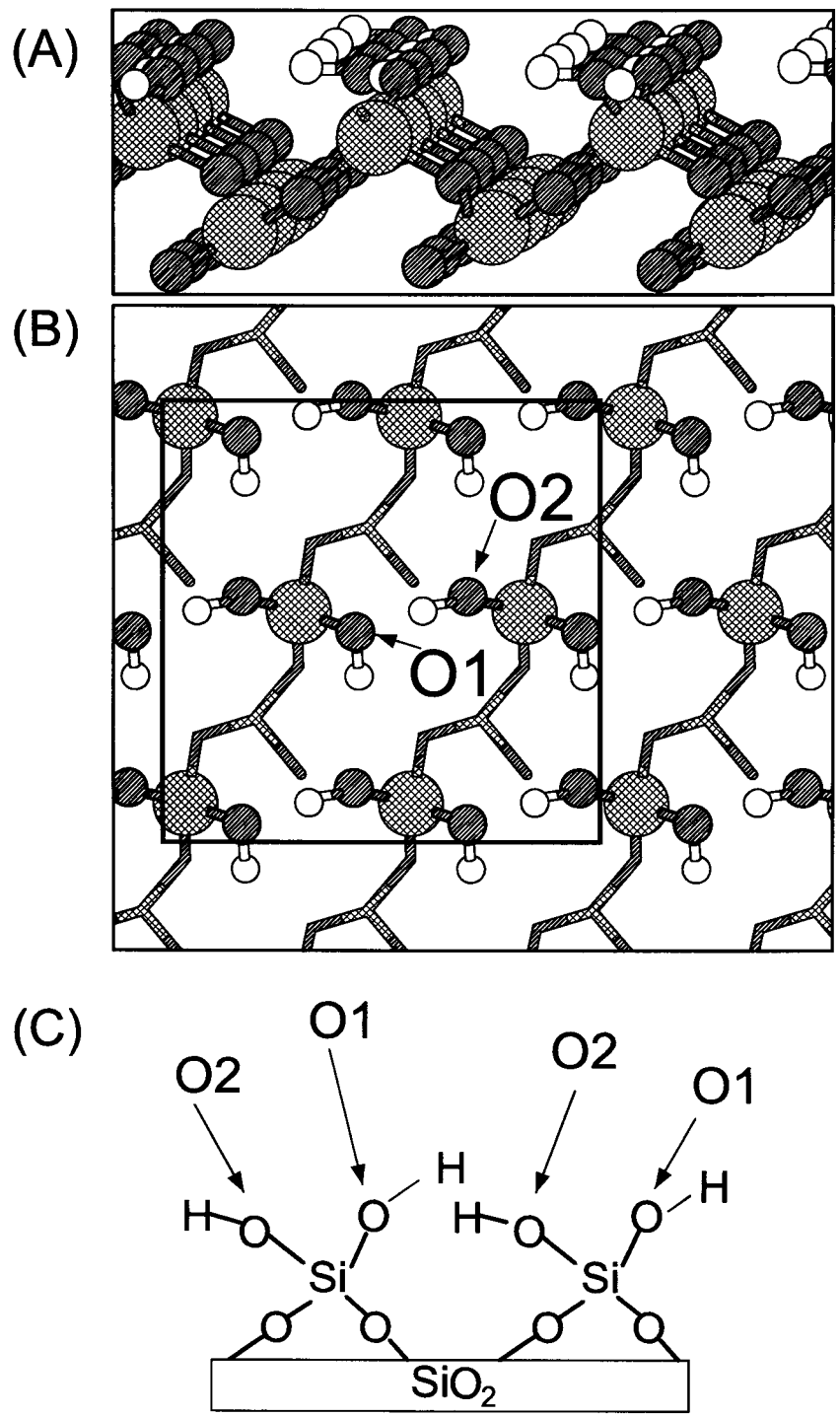
FIGS. 6 (A) and (B) provide the side and top views, respectively, of the hydroxylated $SiO_2$ (001) surface used in the computer simulation of Example 7.

In a 500 ml Schlenk flask 87.5 g (0.6 mol) N-cyclohexylaniline and 131 g (1.0 mol) di-isopropylaminosilane were stirred at ambient temperature under a nitrogen atmosphere for 24 hours. The relatively lower boiling point by-product di-isopropylamine was removed with vacuum at a pressure of 20 mmHg and room temperature (25° C.). The reaction mixture was stirred for another 24 hours. The end-product phenylcyclohexylaminosilane was obtained by vacuum distillation. The end-product was characterized by mass spectroscopy (MS) which is provided in FIG. 5 and shows, among other things, peaks at 205, 178, 162, 132, 115, 93, and 77. The molecular weight of the phenylcyclohexylaminosilane was 205.37.

Example 7

Computer Simulations of Atomic Layer Depositions

A quantum mechanical method based on PM3 using SPARTAN06 simulation package (Wavefunction, Inc., Irvine, Calif.) was used to study the relative chemical stability of several precursors against α-H migration and disproportionation reaction. Using quantum mechanical density functional theory, extensive calculations were conducted using computer modeling software to systematically evaluate the reaction energies of various SiN precursors. The calculations were done under the generalized gradient approximation (GGA) using the exchange-correlation functional proposed by Perdew-Wang (PW91) coupled with the double numerical atomic basis set augmented with polarization functions. All molecular structures were fully optimized to obtain the energetically most favorable geometries. The precursors used in the computer analysis are as follows: dimethylaminosilane (DMAS) and the precursor having Formula I described herein or phenylmethylaminosilane (PMAS).

For this computer simulation, the reconstructed and fully hydroxylated $SiO_2$ (001) surface was modeled with a slab containing 6-layers alternated with two layers of O atoms and one layer of Si atoms, which is the preferred surface orientation for silica (see FIG. 1(A)). The top two layers of O atoms are all terminated by H atoms, representing the fully hydroxylated surface. There is a vacuum between adjacent slabs with 20 Å separation. The selected super cell contains 8 Si atoms, 20 O atoms and 8 H atoms, in addition to a precursor molecule. Prior to the precursor deposition, the surface was fully equilibrated. The optimized main structural parameters, shown in Table 2, are in good agreement with the experimental values and previous DFT calculations.

A simulated atomic layer deposition process to develop a $SiO_2$ film using a Si precursor takes two successive steps. In the first step, a silicon precursor is vaporized and then introduced onto a hydroxylated Si surface. Subsequently, reaction occurs on the surface with Si attacking the surface O on the hydroxyl group and the H of the hydroxyl group attacks the amino group of the precursor. The reaction leads to formation of a surface Si—O bond and liberation of an amine molecule into the gas-phase. In the second step, an oxygen source such as $O_3$ or $O_2$ molecules are introduced to oxidize the Si—H bonds. These steps would lead to growth of one layer of $SiO_2$ film. The oxidation step is kinetically very fast and highly exothermic. Therefore, one important step to consider in the ALD process is Si precursor deposition. Different precursors give rise to very different quality of $SiO_2$ films.

Figure 7:
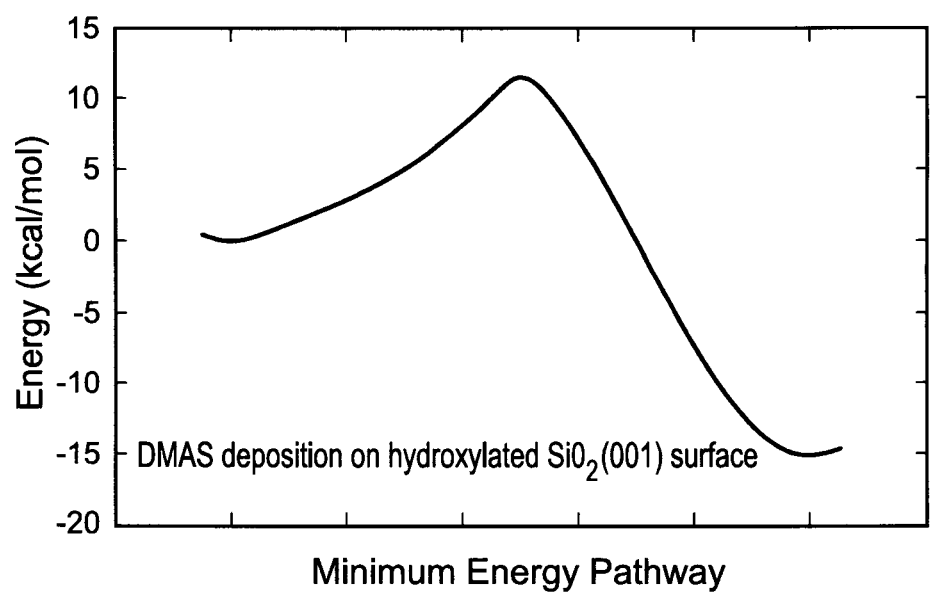
FIG. 7 provides the calculated energy profile of minimum energy pathway for deposition of dimethylaminosilane (DMAS) on hydroxylated $SiO_2$(001) surface in the computer simulation presented in Example 7.

The first principles DFT calculations were performed to investigate the minimum energy pathway of DMAS deposition on the fully hydroxylated $SiO_2$(001) surface. The calculated energy profile is shown in FIG. 7. The simulation yields a thermochemical energy of −15.1 kcal/mol and activation barrier of 11.5 kcal/mol. The results suggest that DMAS is a reactive precursor and can be deposited on the surface with favorable thermodynamics and a low activation barrier. However, DMAS is not thermally stable and can readily undergo the following disproportionational reaction at ambient conditions:

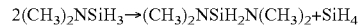

$2(CH_3)_2NSiH_3 \rightarrow (CH_3)_2NSiH_2N(CH_3)_2 + SiH_4$

The calculated thermochemical energy and activation barrier for this reaction are −0.6 kcal/mol and 5.4 kcal/mol, respectively. While the reaction is essentially thermochemically neutral, the exceedingly low activation barrier promotes the disproportionational reaction at room temperature, indicating DMAS is not stable.

Figure 8:
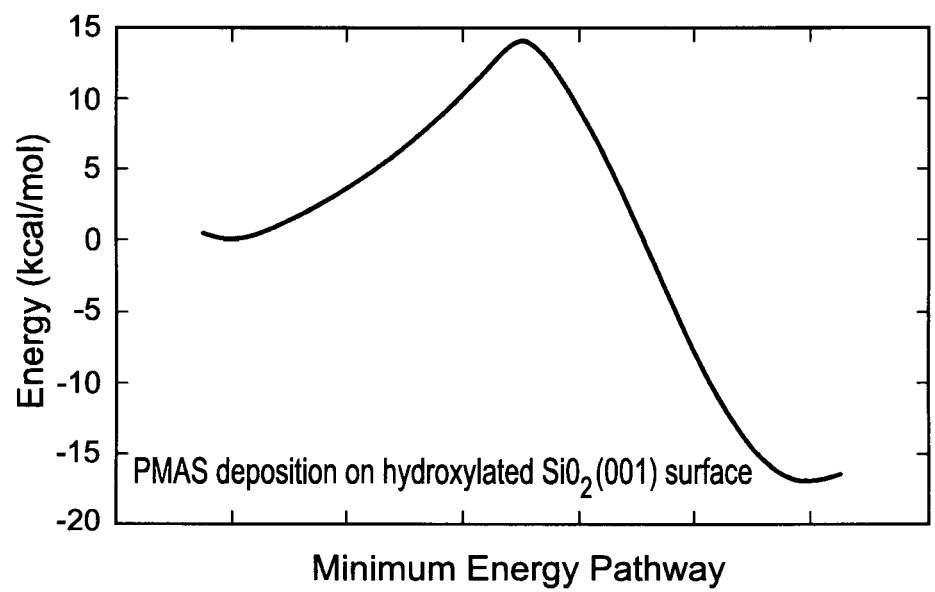
FIG. 8 provides the calculated energy profile of minimum energy pathway for deposition of phenylmethylaminosilane (PMAS) on hydroxylated $SiO_2$(001) surface in the computer simulation presented in Example 7.

The first principles DFT calculations were performed to investigate the minimum energy pathway of DMAS deposition on the fully hydroxylated $SiO_2$(001) surface. The calculated energy profile is shown in FIG. 8. The simulation yields a thermochemical energy of −16.9 kcal/mol and activation barrier of 14.1 kcal/mol. The results suggest that PMAS has an activation barrier only approximately 2.6 kcal/mol higher than that of DMAS. However, it is thermochemically much more exothermic. The results of the computer simulation indicate that PMAS can be deposited on the surface with favorable thermodynamics and a low activation barrier.

TABLE 2

The selected bond parameters compared with reported values

| Bond parameters | In this study | Ref. 12 | EXPT[12] |
|---|---|---|---|
| r(O—H)/Å | 0.98 | 0.98 | — |
| r(Si—O)/A | 1.60 | 1.64 | 1.60 |
|  | 1.66 | 1.66 | 1.61 |
| ∠(O—H—O) | 166.9 | 165.8 | — |
|  | 175.8 | 172.0 | — |
| ∠(Si—O—H) | 112.0 | 113.0 | — |

Example 8

Atomic Layer Deposition of Silicon Oxide Films

Atomic layers depositions of silicon oxide films were conducted using the organoaminosilane precursor phenylmethylaminosilane (PMAS) to verify the results of the computer simulation in Example 7. The depositions were performed on a laboratory scale ALD processing tool starting at 150° C. and temperatures were reduced until room temperature or the precursor failed to generate an oxide film. The process steps that were used to deposit the $SiO_2$ films are shown in Table 3. Depositions were performed using a baseline of 500 cycles with ozone as the oxygen source gas and the process parameters of the depositions are provided in Table 3.

TABLE 3

| | | Process for Generating Basic ALD Oxide Films with $O_3$ | | |
|---|---|---|---|---|
| Step 1 | 6 seconds (sec) | Nitrogen Purge of Reactor | Flow 1.5 slpm $N_2$ | Purges out unreacted chemical from reactor |
| Step 2 | 6 sec | Chamber evacuation | <100 mT | Preps the reactor for the precursor dose |
| Step 3 | 2 sec | Close throttle valve | | Increases precursor resonance time |
| Step 4 | variable | Dose Silicon Precursor | | Reactor pressure typically <1T during dose |
| Step 5 | 6 sec | Nitrogen Purge of Reactor | Flow 1.5 slpm $N_2$ | Purges out unreacted chemical from reactor |
| Step 6 | 6 sec | Chamber evacuation | <100 mT | Preps the reactor for the precursor dose |
| Step 7 | 2 sec | Close throttle valve | | Increases precursor resonance time |
| Step 8 | 2 sec | Dose Ozone | | $O_3$ at 15-17% post generator, P = <8T |

The resultant $SiO_2$ films were characterized for deposition rate, refractive index and % non-uniformity. In Table 4, the refractive index of the films was measured using a FilmTek 2000SE ellipsometer by fitting the reflection data from the film to a pre-set physical model (e.g., the Lorentz Oscillator model). For refractive index, a value of around 1.44 to 1.47 would reflect a typical CVD silicon oxide film. All of the precursors tested deposited films having a refractive index of ranging from about 1.4 to about 1.5. The % non-uniformity quoted was obtained from a 9-point map using the standard equation: % non-uniformity=((max−min)/(2*mean)).

TABLE 4

| | ALD Deposition Results | | | | |
|---|---|---|---|---|---|
| Film No. | Precursor | Wafer Temp | Dep Rate (Å/cycle) | Refractive Index | % Non-uniformity |
| 1 | PMAS | 150 | 0.848 | 1.443 | 1.57 |
| 2 | PMAS | 100 | 1.144 | 1.4545 | 1.57 |
| 3 | PMAS | 75 | 0.828 | 1.4697 | 13.78 |
| 4 | PMAS | 50 | 1.004 | 1.4507 | 6.67 |
| 5 | PMAS | 23 | 0.382 | 1.5547 | 3.14 |

Example 9

Comparison of Atomic Layer Deposition of Silicon Oxide Films

Figure 9:
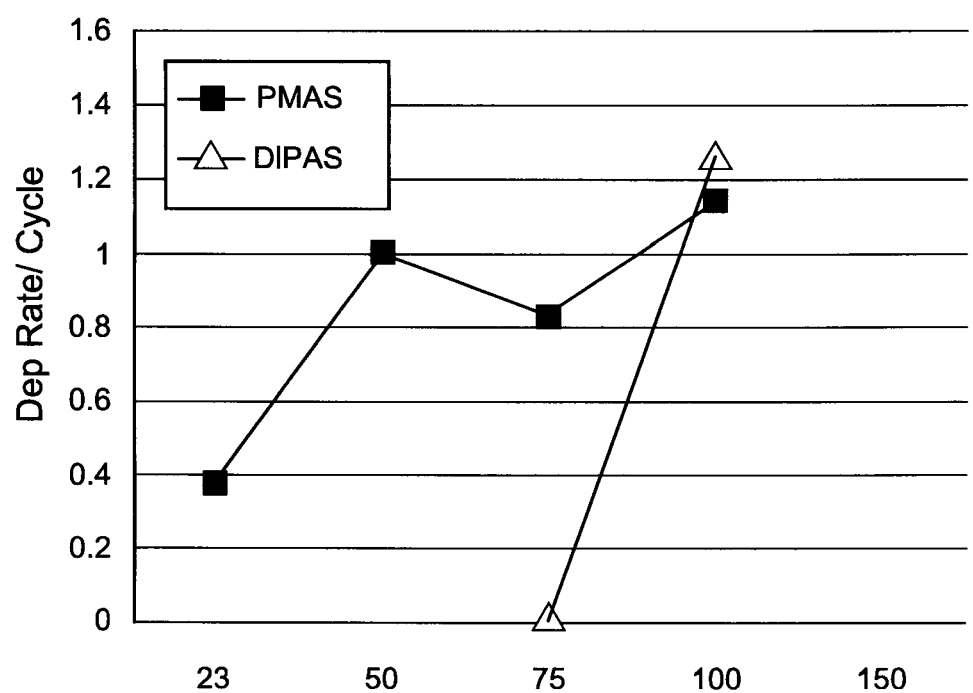
FIG. 9 provides a comparison of the deposition rate versus temperature for silicon oxide films deposited using either PMAS and diisopropylaminosilane (DIPAS) as the organoaminosilane precursor described in Example 9.
Figure 10:
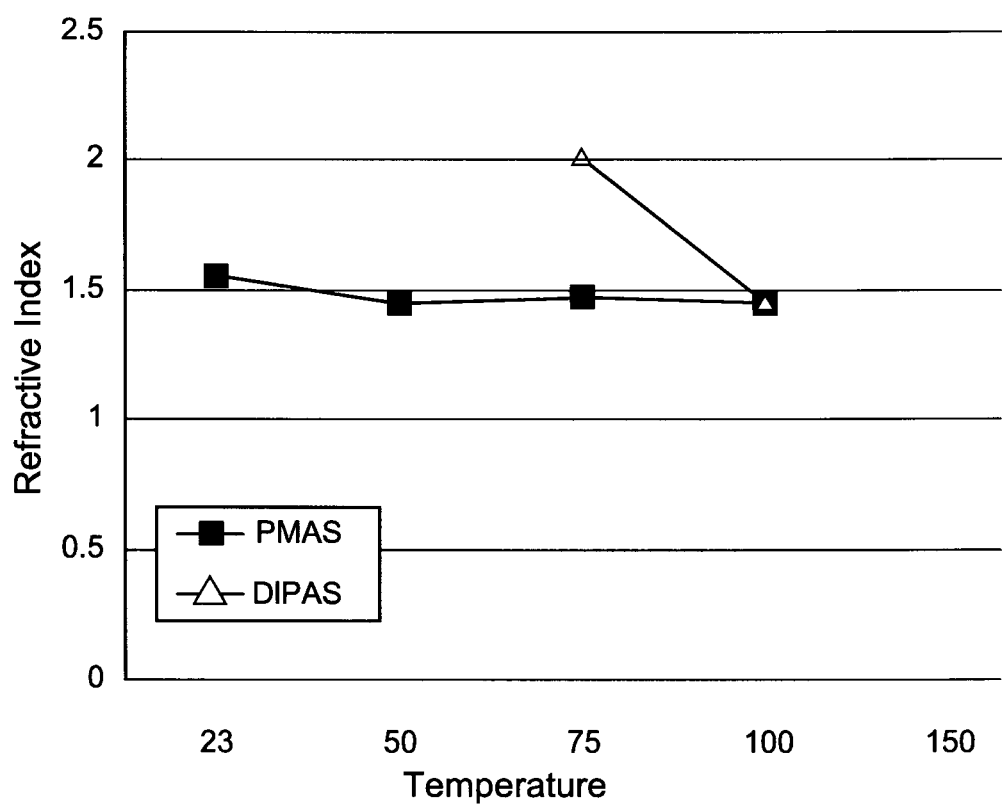
FIG. 10 provides a comparison of the refractive index versus temperature for silicon oxide films deposited using either PMAS and diisopropylaminosilane (DIPAS) as the organoaminosilane precursor described in Example 9.

Atomic layers depositions of silicon oxide films were conducted using the organoaminosilane precursors phenylmethylaminosilane (PMAS), and diisopropylaminosilane (DIPAS) using the ALD process described in Table 3. The depositions were performed on a laboratory scale ALD processing tool at the temperatures shown on the y axis of FIG. 9 (e.g., 23° C. or room temperature, 50° C., 75° C., and 100° C.). The resultant silicon oxide films were characterized for deposition rate/cycle, and refractive index and the results are also provided in FIGS. 9 and 10. In FIG. 9, the deposition rate per cycle is measured as Angstroms (Å)/cycle. In FIG. 10, the refractive index of the films was measured using a FilmTek 2000SE ellipsometer by fitting the reflection data from the film to a pre-set physical model (e.g., the Lorentz Oscillator model). As previously mentioned, for refractive index, a value of around 1.44 to 1.47 would reflect a typical CVD silicon oxide film.

FIGS. 9 and 10 provide the relative deposition results and refractive indices for ALD deposited silicon oxide films using the two precursors. FIG. 9 shows that for the same process conditions and ozone exposure time, PMAS appears to be in an ALD process window through 50° C. FIG. 9 also shows that DIPAS did not deposit films below 100° C. under the process conditions used in the example. FIG. 10 indicates that both DIPAS and PMAS precursors yield silicon oxide films with good refractive indices for ALD oxide at around 100° C. However, for silicon oxide films deposited using DIPAS at 75° C., the refractive index for the film then increases, possibly due to impurities in the film (carbon containing ligands).

Example 10

Deposition of Silicon Nitride Films Using Organoaminosilane Precursors

The organoaminosilane precursor phenylmethylaminosilane was investigated for its effect as a silicon source on the deposition process to form silicon nitride films and the properties of the thin films deposited. The thin film deposition was performed using a LPCVD horizontal furnace or an ATV PEO 612 furnace. The working pressure for the deposition was ~1 Torr and deposition temperature was at 570° C. and 650° C. (see Table 6). $NH_3$ was used as the nitrogen source. The PMAS precursor was delivered to the furnace using vapor draw and line temperatures that were adjusted based on the varying vapor pressures for the different precursor materials. The process parameters for the deposition are provided in Table 6.

Wafers from each run were analyzed for basic film properties and the results for each precursor are provided in Table 7. In Table 7, the refractive index of the dielectric films was measured using a FilmTek 2000SE ellipsometer by fitting the reflection data from the film to a pre-set physical model (e.g., the Lorentz Oscillator model). For refractive index, a value of around 1.9 to 2.0 would reflect a typical CVD silicon nitride film. All of the precursors tested had deposited films having a refractive index of approximately 1.8 or higher. The % non-uniformity quoted was obtained from a 9-point map using the standard equation: % non-uniformity=((max−min)/(2*mean)).

The characterization of the chemical composition of silicon nitride films deposited using the phenylmethylaminosilane precursor was performed using a Physical Electronics 5000VersaProbe XPS Spectrometer, which is equipped with multi-channel plate detectors (MCD) and an Al monochromatic X-ray source and the results are also presented in Table 7.

TABLE 5

Process Parameters for CVD Deposition

| Precursor | RUN # | Temp. °C. | Pressure (mTorr) | PMAS flow (sccm) | $NH_3$ flow (sccm) | Time (min.) |
|---|---|---|---|---|---|---|
| Phenylmethyl-aminosilane (PMAS) | 787 | 570 | 1000 | 11.9 | 10.5 | 110 |
| Phenylmethyl-aminosilane (PMAS) | 789 | 650 | 1000 | 17.9 | 10.5 | 180 |

TABLE 6

CVD silicon nitride comparison

| Precursor | RUN # | Dep. rate (Å) | Average d (Å) | RI | % Non-uniformity |
|---|---|---|---|---|---|
| Phenylmethylaminosilane (PMAS) | 787 | 12.6 | 1386 | 1.79 | 6.6 |
| Phenylmethylaminosilane (PMAS) | 789 | 36.5 | 6574 | 2.15 | 17.9 |

TABLE 7

Atomic concentrations for various CVD silicon nitride films (relative %)

| Precursor | RUN # | C | N | O | Si |
|---|---|---|---|---|---|
| Phenylmethylaminosilane (PMAS) | 787 | 62.29 | 11.31 | 6.56 | 19.84 |
| Phenylmethylaminosilane (PMAS) | 789 | 63.76 | 9.57 | 7.5 | 19.17 |

Example 11

PEALD Silicon Nitride Using Phenylmethylaminosilane as Silicon Source and Ammonia Plasma as Nitrogen-Containing Source Silicon nitride films were deposited using a laminar flow reactor (CNT Savannah 100) with a remote plasma system installed (AE systems). A typical ALD cycle consists of the following steps. Phenylmethylaminosilane was kept at 70° C. and delivered via bubbling with 10 sccm nitrogen as carrier gas into the reactor. The dose time of N-methylanilinylsilane was in range from 0.05 sec to 5 sec; was purged with inert gas and then pumped down to baseline vacuum; introducing ammonia plasma with a flow rate of 5 sccm through the plasma generator set at 0.9 KW power and then into the wafer surface by opening a slit valve directly over the wafer, with exposures ranging from 2 to 9 seconds; and purged with inert gas and evacuated to baseline vacuum. The cycle was repeated until a desired thickness was achieved.

In one experiment, silicon nitrogen film was deposited with the following ALD conditions: wafer temperature and 270° C.; phenylmethylaminosilane 0.5 sec; 8 sec nitrogen purge and 6 sec dynamic evacuation; ammonia plasma exposure, 9 sec; 8 sec nitrogen purge and 6 sec dynamic evacuation. The cycle was repeated 1000 times. The refractive index of resulting film was 2.04, a typical value for silicon nitride films.

Example 12

Comparison of Thermal Stability

Figure 11:
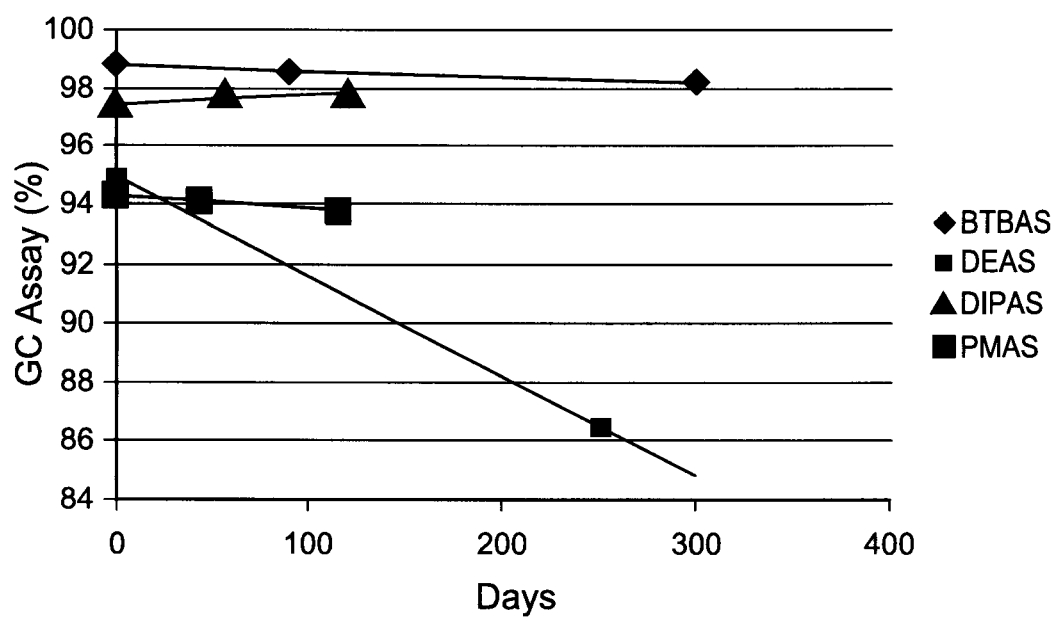
FIG. 11 provides a comparison of the stability of various organoaminosilanes precursors, e.g., bistertbutylaminosilane (BTBAS), diethylaminosilane (DEAS), DIPAS, and PMAS, as measured by gas chromatography assay as described in Example 12.

A sample of phenylmethylaminosilane (PMAS) was loaded into a quartz bubbler at 55-60° C. and kept for approximately 5 weeks. A gas chromatography (GC) analysis of the sample indicates that there is almost no degradation after this time period. Another sample of phenylmethylaminosilane was loaded in a glass vial and kept for 115 days at room temperature inside a glove box. GC analysis indicates less than 0.5% degradation. Similar glove box testing was run for the following organoaminosilanes: PMAS, bistertbutylaminosilane (BTBAS), diethylaminosilane (DEAS), and diisopropylaminosilane (DIPAS) and the results of the testing is provided in FIG. 11. BTBAS has been employed to deposit silicon nitride and oxide in the semi-conductor industries since 2000. FIG. 11 shows that PMAS exhibits similar stability to BTBAS and DIPAS. By contrast, DEAS showed significant degradation. The stability results suggests that phenylmethylaminosilane is thermally stable and suitable as organoaminosilane precursor for semi-conductor processes.

The invention claimed is:

1. An organoaminosilane precursor represented by the following formula I:

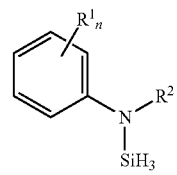

I wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from, a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_7$ to $C_{10}$ aryl group, a linear or branched $C_1$ to $C_6$ fluorinated alkyl group, and a $C_4$ to $C_{10}$ cyclic alkyl group.

2. The organoaminosilane precursor of claim 1 wherein the $R^1$ and $R^2$ are linked to together to form a ring.

3. The organoaminosilane precursor of claim 1 wherein $R^1$ and $R^2$ are the same.

4. The organoaminosilane precursor of claim 1 wherein $R^1$ and $R^2$ are different.

5. The organoaminosilane precursor of claim 1 comprising at least one selected from the group consisting of phenylmethylaminosilane, phenylethylaminosilane, phenyl-iso-propylaminosilane, phenylallylaminosilane, m-tolylmethylaminosilane, N-silyl-tetrahydroquinoline, N-silyl-3-anilinopropionitrile, N-silyl-N-phenylglycinonitrile, N-silylcarbazole, phenylcyclohexylaminosilane, N-silyl-2-methylindoline, N-silylbenzomorpholine, N-silylindole, N-silyl-2-methylindole, N-silyl-3-methylindole, o-tolylethylaminosilane, p-tolylethylaminosilane, m-tolylethylaminosilane, p-tolylethylaminosilane, o-tolylethylaminosilane, and N-silyl-1,2,3,4-Tetrahydro-2-methylquinoline.

6. The organoaminosilane precursor of claim 5 comprising phenylmethylaminosilane.

7. The organoaminosilane precursor of claim 5 comprising phenylethylaminosilane.

8. The organoaminosilane precursor of claim 5 comprising m-tolylethylaminosilane.

9. An organoaminosilane precursor represented by the following formula I:

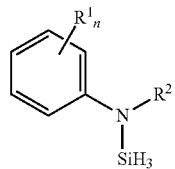

I wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a hydrogen atom, a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_6$ to $C_{10}$ aryl group, a linear or branched $C_1$ to $C_6$ fluorinated alkyl group, and a $C_4$ to $C_{10}$ cyclic alkyl group, wherein the organoaminosilane precursor comprises at least one selected from the group consisting of phenylmethylaminosilane, phenylethylaminosilane, phenyl-iso-propylaminosilane, phenylallylaminosilane, m-tolylmethylaminosilane, N-silyl-tetrahydroquinoline, N-silyl-3-anilinopropionitrile, N-silyl-N-phenylglycinonitrile, N-silylcarbazole, phenylcyclohexylaminosilane, N-silyl-2-methylindoline, N-silylbenzomorpholine, N-silylindole, N-silyl-2-methylindole, N-silyl-3-methylindole, o-tolylethylaminosilane, p-tolylethylaminosilane, m-tolylethylaminosilane, p-tolylethylaminosilane, o-tolylethylaminosilane, and N-silyl-1,2,3,4-Tetrahydro-2-methylquinoline.

10. The organoaminosilane precursor of claim 9 comprising phenylmethylaminosilane.

11. The organoaminosilane precursor of claim 9 comprising phenylethylaminosilane.

12. The organoaminosilane precursor of claim 9 comprising m-tolylethylaminosilane.

13. A method for forming a dielectric film on at least one surface of a substrate by a deposition process chosen from a chemical vapor deposition process and an atomic layer deposition process, the method comprising:
providing the at least one surface of the substrate in a reaction chamber;
introducing at least one organoaminosilane precursor having the following formula I in the reactor:

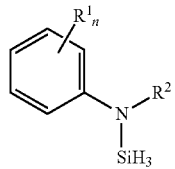

I wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_7$ to $C_{10}$ aryl group, a linear or branched $C_1$ to $C_6$ fluorinated alkyl group, and a $C_4$ to $C_{10}$ cyclic alkyl group;
introducing a nitrogen-containing source into the reactor wherein the at least one organoaminosilane precursor and the nitrogen-containing source react to the dielectric films on the at least one surface.

14. The method of claim 13 wherein the at least one organoaminosilane precursor is selected from the group consisting of phenylmethylaminosilane, phenylethylaminosilane, phenyl-iso-propylaminosilane, phenylallylaminosilane, m-tolylmethylaminosilane, N-silyl-tetrahydroquinoline, N-silyl-3-anilinopropionitrile, N-silyl-N-phenylglycinonitrile, N-silylcarbazole, phenylcyclohexylaminosilane, N-silyl-2-methylindoline, N-silylbenzomorpholine, N-silylindole, N-silyl-2-methylindole, N-silyl-3-methylindole, o-tolylethylaminosilane, p-tolylethylaminosilane, m-tolylethylaminosilane, p-tolylethylaminosilane, o-tolylethylaminosilane, and N-silyl-1,2,3,4-Tetrahydro-2-methylquinoline.

15. The method of claim 14 wherein the at least one organoaminosilane precursor comprises phenylmethylaminosilane.

16. The method of claim 14 wherein the at least one organoaminosilane precursor comprises phenylethylaminosilane.

17. The method of claim 14 wherein the at least one organoaminosilane precursor comprises m-tolylethylaminosilane.

18. The method of claim 13 wherein the nitrogen-containing source is selected from the group consisting of ammonia, hydrazine, monoalkylhydrazine, dialkylhydrazine, nitrogen, nitrogen/hydrogen, ammonia plasma, nitrogen plasma, nitrogen/hydrogen plasma, and mixtures thereof.

19. The method of claim 13 wherein the dielectric film is selected from the group consisting of silicon nitride and silicon carbonitride.

20. A method of forming a dielectric film via an atomic layer deposition (ALD) process, the method comprising the steps of:
a. providing a substrate in an ALD reactor;
b. providing in the ALD reactor an at least one organoaminosilane precursor having the following formula I:

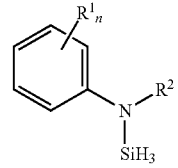

I wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_7$ to $C_{10}$ aryl group, a linear or branched $C_1$ to $C_6$ fluorinated alkyl group, and a $C_4$ to $C_{10}$ cyclic alkyl group;
    c. purging the ALD reactor with an inert gas;
    d. providing a nitrogen-containing source in the ALD reactor;
    e. purging the ALD reactor with an inert gas; and
    f. repeating the steps b through e until a desired thickness of the dielectric film is obtained.

21. The method of claim 20 wherein the at least one organoaminosilane precursor is selected from the group consisting of phenylmethylaminosilane, phenylethylaminosilane, phenyl-iso-propylaminosilane, phenylallylaminosilane, m-tolylmethylaminosilane, N-silyl-tetrahydroquinoline, N-silyl-3-anilinopropionitrile, N-silyl-N-phenylglycinonitrile, N-silylcarbazole, phenylcyclohexylaminosilane, N-silyl-2-methylindoline, N-silylbenzomorpholine, N-silylindole, N-silyl-2-methylindole, N-silyl-3-methylindole, o-tolylethylaminosilane, p-tolylethylaminosilane, m-tolylethylaminosilane, p-tolylethylaminosilane, o-tolylethylaminosilane, and N-silyl-1,2,3,4-Tetrahydro-2-methylquinoline.

22. The method of claim 21 wherein the at least one organoaminosilane precursor comprises phenylmethylaminosilane.

23. The method of claim 21 wherein the at least one organoaminosilane precursor comprises phenylethylaminosilane.

24. The method of claim 21 wherein the at least one organoaminosilane precursor comprises m-tolylethylaminosilane.

25. The method of claim 20 wherein the nitrogen-containing source is selected from the group consisting of ammonia, hydrazine, monoalkylhydrazine, dialkylhydrazine, nitrogen, nitrogen/hydrogen, ammonia plasma, nitrogen plasma, nitrogen/hydrogen plasma, and mixtures thereof.

26. The method of claim 20 wherein the dielectric film is selected from the group consisting of silicon nitride and silicon carbonitride.

27. A method of forming a dielectric film onto at least a surface of a substrate using a plasma enhanced atomic layer deposition (PEALD) process, the method comprising:
    a. providing a substrate in an ALD reactor;
    b. providing in the ALD reactor an at least one organoaminosilane precursor having the following formula I:

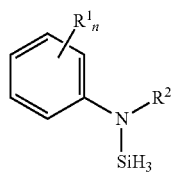

wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_7$ to $C_{10}$ aryl group, a linear or branched $C_1$ to $C_6$ fluorinated alkyl group, and a $C_4$ to $C_{10}$ cyclic alkyl group;
    c. purging the ALD reactor with an inert gas;
    d. providing a plasma nitrogen-containing source in the ALD reactor;
    e. purging the ALD reactor with an inert gas; and
    f. repeating the steps b through e until a desired thickness of the dielectric film is obtained.

28. The method of claim 27 wherein the at least one organoaminosilane precursor is selected from the group consisting of phenylmethylaminosilane, phenylethylaminosilane, phenyl-iso-propylaminosilane, phenylallylaminosilane, m-tolylmethylaminosilane, N-silyl-tetrahydroquinoline, N-silyl-3-anilinopropionitrile, N-silyl-N-phenylglycinonitrile, N-silylcarbazole, phenylcyclohexylaminosilane, N-silyl-2-methylindoline, N-silylbenzomorpholine, N-silylindole, N-silyl-2-methylindole, N-silyl-3-methylindole, o-tolylethylaminosilane, p-tolylethylaminosilane, m-tolylethylaminosilane, p-tolylethylaminosilane, o-tolylethylaminosilane, and N-silyl-1,2,3,4-Tetrahydro-2-methylquinoline.

29. The method of claim 28 wherein the at least one organoaminosilane precursor comprises phenylmethylaminosilane.

30. The method of claim 28 wherein the at least one organoaminosilane precursor comprises phenylethylaminosilane.

31. The method of claim 28 wherein the at least one organoaminosilane precursor comprises m-tolylethylaminosilane.

32. The method of claim 27 wherein the nitrogen-containing source is selected from the group consisting of ammonia, hydrazine, monoalkylhydrazine, dialkylhydrazine, nitrogen, nitrogen/hydrogen, ammonia plasma, nitrogen plasma, nitrogen/hydrogen plasma, and mixtures thereof.

33. The method of claim 27 wherein the dielectric film is selected from the group consisting of silicon nitride and silicon carbonitride.

34. A method for forming a silicon oxide film on a substrate comprising:
    reacting an oxidizing agent with a precursor comprising an organoaminosilane represented by the following formula I:

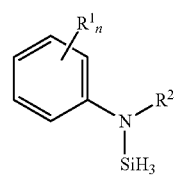

wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_7$ to $C_{10}$ aryl group, a linear or branched $C_1$ to $C_6$ fluorinated alkyl group, and a $C_4$ to $C_{10}$ cyclic alkyl group.

35. The method of claim 34 wherein the vapor deposition is at least one selected from the group consisting of at least one selected from chemical vapor deposition, low pressure vapor deposition, plasma enhanced chemical vapor deposition, cyclic chemical vapor deposition, plasma enhanced cyclic chemical vapor deposition, atomic layer deposition, and plasma enhanced atomic layer deposition.

36. The method of claim 34 wherein the at least one organoaminosilane precursor is selected from the group consisting of phenylmethylaminosilane, phenylethylaminosilane, phenyl-iso-propylaminosilane, phenylallylaminosilane, m-tolylmethylaminosilane, N-silyl-tetrahydroquinoline, N-silyl-3-anilinopropionitrile, N-silyl-N-phenylglycinonitrile, N-silylcarbazole, phenylcyclohexylaminosilane, N-silyl-2-methylindoline, N-silylbenzomorpholine, N-silylindole, N-silyl-2-methylindole, N-silyl-3-methylindole, o-tolylethylaminosilane, p-tolylethylaminosilane, m-tolylethylaminosilane, p-tolylethylaminosilane, o-tolylethylaminosilane, and N-silyl-1,2,3,4-tetrahydro-2-methylquinoline.

37. The method of claim 34 wherein the reacting step is conducted at a temperature of 200° C. or less.

38. The method of claim 34 wherein the reacting step is conducted at a temperature of 100° C. or less.

39. The method of claim 34 wherein the reacting step is conducted at 50° C. or less.

40. A method for forming a silicon oxide film on a substrate comprising:
  forming via vapor deposition of the silicon oxide film on the substrate from a composition comprising at least one organoaminosilane precursor having the following Formula I:

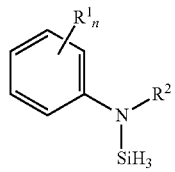

wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_7$ to $C_{10}$ aryl group, a linear or branched $C_1$ to $C_6$ fluorinated alkyl group, and a $C_4$ to $C_{10}$ cyclic alkyl group,
  wherein the vapor deposition is at least one selected from chemical vapor deposition, low pressure vapor deposition, plasma enhanced chemical vapor deposition, cyclic chemical vapor deposition, plasma enhanced cyclic chemical vapor deposition, atomic layer deposition, and plasma enhanced atomic layer deposition.

41. The method of claim 40 wherein the at least one organoaminosilane precursor is selected from the group consisting of phenylmethylaminosilane, phenylethylaminosilane, phenyl-iso-propylaminosilane, phenylallylaminosilane, m-tolylmethylaminosilane, N-silyl-tetrahydroquinoline, N-silyl-3-anilinopropionitrile, N-silyl-N-phenylglycinonitrile, N-silylcarbazole, phenylcyclohexylaminosilane, N-silyl-2-methylindoline, N-silylbenzomorpholine, N-silylindole, N-silyl-2-methylindole, N-silyl-3-methylindole, o-tolylethylaminosilane, p-tolylethylaminosilane, m-tolylethylaminosilane, p-tolylethylaminosilane, o-tolylethylaminosilane, and N-silyl-1,2,3,4-Tetrahydro-2-methylquinoline.

42. The method of claim 40 wherein the reacting step is conducted at a temperature of 200° C. or less.

43. The method of claim 40 wherein the reacting step is conducted at a temperature of 100° C. or less.

44. The method of claim 40 wherein the reacting step is conducted at 50° C. or less.

45. A method for forming a silicon oxide film on a substrate comprising:
  introducing an organoaminosilane represented by the following formula I:

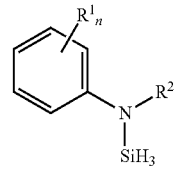

wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_7$ to $C_{10}$ aryl group, a linear or branched $C_1$ to $C_6$ fluorinated alkyl group, and a $C_4$ to $C_{10}$ cyclic alkyl group;
  introducing at least one oxidizing agent into the reactor wherein the at least one oxidizing agent reacts with the organoaminosilane to provide the silicon oxide film on the substrate.

46. A method for forming a silicon oxide film on a substrate wherein the film comprises a thickness, the method comprising:
  a. introducing an at least one organoaminosilane represented by the formula I into a deposition chamber:

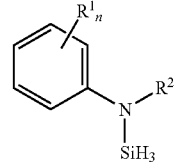

wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_7$ to $C_{10}$ aryl group, a linear or branched $C_1$ to $C_6$ fluorinated alkyl group, and a $C_4$ to $C_{10}$ cyclic alkyl group;
  b. chemisorbing the at least one organoaminosilane precursor onto the substrate;
  c. purging away the unreacted at least one organoaminosilane precursor using a purge gas;
  d. providing an oxygen source to the organoaminosilane precursor onto the heated substrate to react with the sorbed at least one organoaminosilane precursor; and
  e. optionally purging away any unreacted oxygen source.

47. The method of claim 46 wherein steps a. through d. and optional step e. are repeated until the thickness of film is established.

48. The method of claim 46 wherein the at least one organoaminosilane precursor is selected from the group consisting of phenylmethylaminosilane, phenylethylaminosilane, phenyl-iso-propylaminosilane, phenylallylaminosilane, m-tolylmethylaminosilane, N-silyl-tetrahydroquinoline, N-silyl-3-anilinopropionitrile, N-silyl-N-phenylglycinonitrile, N-silylcarbazole, phenylcyclohexylaminosilane, N-silyl-2-methylindoline, N-silylbenzomorpholine, N-silylindole, N-silyl-2-methylindole, N-silyl-3-methylindole, o-tolylethylaminosilane, p-tolylethylaminosilane, m-tolylethylaminosilane, p-tolylethylaminosilane, o-tolylethylaminosilane, and N-silyl-1,2,3,4-Tetrahydro-2-methylquinoline.

49. The method of claim 46 wherein the reacting step is conducted at a temperature of 200° C. or less.

50. The method of claim 45 wherein the reacting step is conducted at a temperature of 100° C. or less.

51. The method of claim 49 wherein the reacting step is conducted at 50° C. or less.

52. The method of claim 46 is an atomic layer deposition process.

53. The method of claim 46 is a plasma enhanced cyclic chemical vapor deposition process.

54. A vessel which is used to deliver a precursor for the deposition of a silicon-containing film, the vessel comprising:
the precursor represented by the following formula I:

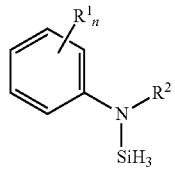

I wherein $R^1$ in formula I is independently selected from a hydrogen atom, a linear or a branched $C_1$ to $C_6$ alkyl group, a linear or a branched $C_2$ to $C_6$ alkenyl group, a linear or a branched $C_2$ to $C_6$ alkynyl group, a $C_1$ to $C_6$ alkoxy group, a $C_1$ to $C_6$ dialkylamino group and an electron withdrawing group and n is a number selected from 0, 1, 2, 3, 4, and 5; and $R^2$ is independently selected from a linear or branched $C_1$ to $C_6$ alkyl group, a linear or a branched $C_2$ to $C_6$ alkenyl group, a linear or branched $C_2$ to $C_6$ alkynyl group, a $C_1$ to $C_6$ alkoxy group, a $C_1$ to $C_6$ alkyl group with a $C_1$ to $C_6$ alkoxy group attached thereto, a $C_1$ to $C_6$ alkyl group with a $C_1$ to $C_6$ dialkylamino group attached thereto, a $C_1$ to $C_6$ dialkylamino group, a $C_7$ to $C_{10}$ aryl group, a linear or branched $C_1$ to $C_6$ fluorinated alkyl group, and a $C_4$ to $C_{10}$ cyclic alkyl group; and wherein the purity of the precursor is about 98% or greater.

55. The vessel of claim 54 wherein the vessel is comprised of stainless steel.

56. An organoaminosilane precursor for depositing a dielectric film comprising at least one compound selected from the group consisting of: phenylmethylaminosilane, phenylethylaminosilane, phenyl-iso-propylaminosilane, phenylallylaminosilane, m-tolylmethylaminosilane, N-silyl-tetrahydroquinoline, N-silyl-3-anilinopropionitrile, N-silyl-N-phenylglycinonitrile, N-silylcarbazole, phenylcyclohexylaminosilane, N-silyl-2-methylindoline, N-silylbenzomorpholine, N-silylindole, N-silyl-2-methylindole, N-silyl-3-methylindole, o-tolylethylaminosilane, p-tolylethylaminosilane, m-tolylethylaminosilane, p-tolylethylaminosilane, o-tolylethylaminosilane, and N-silyl-1,2,3,4-Tetrahydro-2-methylquinoline.

57. The organoaminosilane precursor of claim 56 comprising at least one selected from the group consisting of phenylmethylaminosilane, phenylethylaminosilane, and m-tolylethylaminosilane.

* * * * *